United States Patent
Cohen et al.

(10) Patent No.: US 8,247,227 B2
(45) Date of Patent: Aug. 21, 2012

(54) DENDRITIC CELL PRECURSORS

(75) Inventors: Peter A. Cohen, Chagrin Falls, OH (US); Suyu Shu, Shaker Heights, OH (US); Gary K. Koski, Akron, OH (US); Charles S. Carter, Rockville, MD (US); Laura Carter, legal representative, Rockville, MD (US); Brian J. Czerniecki, Haddonfield, NJ (US)

(73) Assignees: The Cleveland Clinic Foundation, Cleveland, OH (US); Trustees of the University of Pennsylvania, Philadelphia, PA (US); National Institutes of Health, Rockville, MD (US)

( * ) Notice: Subject to any disclaimer, the term of this patent is extended or adjusted under 35 U.S.C. 154(b) by 0 days.

(21) Appl. No.: 11/845,976

(22) Filed: Aug. 28, 2007

(65) Prior Publication Data

US 2010/0272700 A1    Oct. 28, 2010

Related U.S. Application Data

(60) Provisional application No. 60/840,647, filed on Aug. 28, 2006.

(51) Int. Cl.
*C12N 5/00* (2006.01)

(52) U.S. Cl. .................. 435/377; 435/325; 435/375
(58) Field of Classification Search .................. None
See application file for complete search history.

(56) References Cited

OTHER PUBLICATIONS

Bontkes HJ et al. 2002. Expansion of dendritic cell precursors from human CD34+ progenitor cells isolated from healthy donor blood; growth factor combination determines proliferation rate and functional outcome. J Leuk Biol 72: 321-29.*

Nosaka T et al. 1999. STAT5 as a molecular regulator of proliferation, differentiation, and apoptosis in hematopoietic cells. EMBO J 18: 4754-65.*

Diao J et al. 2004. Characterization of distinct conventional and plasmacytoid dendritic cell-committed precursors in murine bone marrow. J Immunol 173: 1826-1833.*

* cited by examiner

*Primary Examiner* — Lora E Barnhart Driscoll
(74) *Attorney, Agent, or Firm* — Tarolli, Sundheim, Covell & Tummino LLP

(57) ABSTRACT

A method of generating a population of dendritic cell (DC) precursors includes obtaining a population of progenitor cells from a subject and culturing the progenitor cells in a culture medium. The culture medium can include Flt3 ligand and interleukin-6 and be free of granulocyte-macrophage colony-stimulating factor.

7 Claims, 26 Drawing Sheets

DENDRITIC CELL PRECURSORS

RELATED APPLICATION

This application claims priority to the filing date of U.S. Provisional Application No. 60/840,647, filed Aug. 28, 2006, the subject matter of which is incorporated herein by reference.

GOVERNMENT RIGHTS

The invention described in this application was supported, at least in part, by United Stated Government Contract No.NIH/NCI RO1 CA89511 and NIH/NCI RO1 CA103946 with the National Heart, Lung and Blood Institute and the National Institutes of Health.

TECHNICAL FIELD

The present invention relates generally to a method of generating a dendritic cell (DC) population from progenitor cells, and more particularly to a method of generating a population of DC precursors from $CD34^{pos}$ progenitor cells.

BACKGROUND OF THE INVENTION

Dendritic cells (DCs) are the most potent antigen (Ag)-presenting cells in the human body and have been employed in many tumor vaccine immunotherapy trials, sometimes with therapeutic impacts. DCs prepared from various sources display a wide range of characteristics in vitro and in vivo, and it remains uncertain as to which characteristics are most likely to promote successful immunotherapy.

In vitro, DC phenotypic maturation can be induced by a variety of agents, including CD40 ligand and toll-like receptor (TLR) agonists. The stimulatory effects of such agents, however, fall short of the DCs' potential to achieve DC1 polarization, the maximally effective state for promoting cell-mediated immunity.

The number of circulating DC precursors may be augmented by stem cell mobilizing treatments, notably granulocyte-macrophage colony-stimulating factor (GMCSF), granulocyte colony-stimulating factor (GCSF), Flt3 ligand (Flt3-L), and Flt3-L+GMCSF; however, the potential of such mobilized precursors to achieve DC1 polarization is unclear. For example, Flt3-L+GMCSF treatment induces abundant infiltration of DCs into mouse tumors, but such DCs retain an immature phenotype, activate regulatory T cells, and promote tumor growth. Because immunosuppressive factors such as IL-10, TGF-β, VEGF and $PGE_2$ are often produced within the tumor milieu, such factors may prevent mobilized precursors from attaining maturation and DC1 polarization. Additionally, proliferative treatments themselves may negatively influence the later differentiation response of mobilized DC precursors.

SUMMARY OF THE INVENTION

The present invention relates to a method of generating a population of dendritic cell (DC) precursors. The method includes obtaining a population of progenitor cells from a subject. The progenitor cells are then cultured in a culture medium. The culture medium includes Flt3 ligand (Flt3-L) and interleukin-6 (IL-6) and is free of granulocyte-macrophage colony-stimulating factor (GMCSF). The progenitor cells can include $CD34^{pos}$ cells and be conditioned in the culture medium for a time and under conditions sufficient to allow the progenitor cells to differentiate into a population of DC precursors having a surface marker phenotype $B220^{pos}/CD11c^{neg}/MHC\ Class\ II^{neg}/CD45RA^{pos}$.

In an aspect of the invention, the culture medium can further include one or more cytokine and/or growth factor selected from the group consisting of SCF, IL-3, IL-4, TNF-α, TNF-β, LT-β, IL-2, IL-7, IL-9, IL-15, IL-13, IL-5, IL-1α, IL-1βIFN-γ, IL-10, IL-17, IL-16, IL-18, HGF, IL-11, MSP, FasL, TRAIL, TRANCE, TWEAK, CD27L, CD30L, CD40L, APRIL, TALL-1, 4-1BBL, OX40L, GITRL, IGF-1, IGF-II, MSP, FGF-α, FGF-β, FGF-3-19, NGF, BDNF, NTs, Tpo, Epo, Ang1-4, PDGF-AA, PDGF-BB, VEGF-A, VEGF-B, VEGF-C, VEGF-D, PIGF, EGF, TGF-α, AR, BTC, HRGs, HG-EGF, SMDF, OB, CT-1, CNTF, OSM, MK, PTN, or their functional, recombinant, chemical equivalent, homologue, and combinations thereof. For example, the culture medium include Flt3-L, SCF, IL-6 and a STAT5 antagonist.

The present invention also relates to an isolated population of DC precursors. The DC precursors can have a surface marker phenotype $B220^{pos}/CD11c^{neg}/MHC\ Class\ II^{neg}/CD45RA^{pos}$.

The present invention further relates to a method of developing a mature DC population. The method includes obtaining a population of progenitor cells from a subject. The progenitor cells are cultured in a culture medium. The culture medium includes Flt3-L and IL-6 and is free of GMCSF. The progenitor cells are conditioned in the culture medium for a time and under conditions sufficient to allow the progenitor cells to differentiate into a population of DC precursors having a surface marker phenotype $B220^{pos}/CD11^{neg}/MHC\ Class\ II^{neg}/CD45RA^{pos}$. A mature DC population is then generated from the DC precursors.

In an aspect of the invention, the step of generating the mature DC population further comprises culturing the DC precursors in a culture medium containing at least one agent capable of promoting maturation of the DC precursors into the mature DC population. The agent can be selected from the group consisting of a cytokine, a growth factor, a toll-like receptor agonist, a CD40 ligand, a calcium ionophore, a tumor-derived immunosuppressive factor, a tumor cell, and tumor cell lysate.

In an aspect of the invention, the culture medium can further include one or more cytokine and/or growth factor selected from the group consisting of SCF, IL-3, IL-4, TNF-α, TNF-β, LT-β, IL-2, IL-7, IL-9, IL-15, IL-13, IL-5, IL-1α, IL-1β, IFN-γ, IL-10, IL-17, IL-16, IL-18, HGF, IL-11, MSP, FasL, TRAIL, TRANCE, TWEAK, CD27L, CD30L, CD40L, APRIL, TALL-1, 4-1BBL, OX40L, GITRL, IGF-1, IGF-II, MSP, FGF-α, FGF-β, FGF-3-19, NGF, BDNF, NTs, Tpo, Epo, Ang1-4, PDGF-AA, PDGF-BB, VEGF-A, VEGF-B, VEGF-C, VEGF-D, PIGF, EGF, TGF-α, AR, BTC, HRGs, HG-EGF, SMDF, OB, CT-1, CNTF, OSM, MK, PTN, or their functional, recombinant, chemical equivalent, homologue, and combinations thereof. For example, the culture medium include Flt3-L, SCF, IL-6 and a STAT5 antagonist.

In a still further aspect, the step of generating the mature DC population includes the step of providing at least one agent to promote DC1 polarization. The at least one agent can be selected from the group consisting of TLR agonists, cytokines, and growth factors.

The present invention further relates to a method of treating a subject. The method includes obtaining a population of progenitor cells from a subject. The progenitor cells are cultured in a culture medium. The culture medium includes Flt3-L and IL-6 and is free of GMCSF. The mature DC population is generated from the DC precursors. The mature DC population is co-cultured with at least one tumor-tolerized T cell to produce a population of tolerized T cells. The population of tolerized T cells is administered to the subject.

In an aspect of the invention, the progenitor cells can be conditioned in the culture medium for a time and under conditions sufficient to allow the progenitor cells to differentiate into a population of DC precursor cells having a surface marker phenotype $B220^{pos}/CD11c^{neg}/MHC$ Class $II^{neg}$.

The culture medium can further include one or more cytokine and/or growth factor selected from the group consisting of SCF, IL-3, IL-4, TNF-α, TNF-β, LT-β, IL-2, IL-7, IL-9, IL-15, IL-13, IL-5, IL-1α, IL-10, IFN-γ, IL-10, IL-17, IL-16, IL-18, HGF, IL-11, MSP, FasL, TRAIL, TRANCE, TWEAK, CD27L, CD30L, CD40L, APRIL, TALL-1, 4-1BBL, OX40L, GITRL, IGF-1, IGF-II, MSP, FGF-α, FGF-β, FGF-3-19, NGF, BDNF, NTs, Tpo, Epo, Ang1-4, PDGF-AA, PDGF-BB, VEGF-A, VEGF-B, VEGF-C, VEGF-D, PlGF, EGF, TGF-α, AR, BTC, HRGs, HG-EGF, SMDF, OB, CT-1, CNTF, OSM, MK, PTN, or their functional, recombinant, chemical equivalent, homologue, and combinations thereof. For example, the culture medium include Flt3-L, SCF, IL-6 and a STAT5 antagonist. The progenitor cells can include $CD34^{pos}$ cells.

In a still further aspect, the method can include providing at least one agent to promote DC1 polarization, the at least one agent being selected from the group consisting of TLR agonists, cytokines, and growth factors.

The present invention also relates to a method for up-regulating an immune response in a subject. The method comprising administering to the subject an effective amount of a mixture comprising Flt3-L and IL-6 and being free of GMCSF. In an aspect of the invention, a STAT-5 antagonist can be administered in combination with the Flt3-L and IL-6. The STAT-5 antagonist can include an anti-GMCSF agent.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 8A is a series of slides showing individual T cell cultures after 6 day co-culture with DCs (labels indicate prior DC conditioning treatments) or with anti-CD3. Cultures shown also received exogenous IL-2, IL-7 and IL-15. A total of ten different treatments were compared (selected groups shown in FIGS. 8A-B; all groups shown in FIGS. 13A-B). This is representative of three full comparison experiments. FIG. 8B is a graph showing the response of conditioned DCs to adoptive therapy. T cells driven with Flt3-L+IL-6 conditioned DCs are highly effective as adoptive therapy. Five day established MCA-203 subcutaneous tumors were treated i.v. with T cells from MCA-203 bearers after 12 day culture driven by Flt3-L+IL-6 conditioned DCs or by anti-CD3. Conventional non-myelablative total body irradiation (500 cGy) was given as an adjunct prior to T cells. Cure rates were 0/5 (A, no treatment); 2/5 (B, 5 million anti-CD3 driven T cells; 5/5 (C, 5 million Flt3-L+IL-6 DC driven T cells); 5/5 (D, same as C but 2 million T cells). Treatment outcome (A vs. C/D, p1<0.008; A vs. B, p1<0.141; B vs. C/D, p1=0.04). T cell cultures driven by Flt3-L+IL-6 conditioned DCs were also highly effective against more advanced tumors. This is representative of 4 experiments;

FIG. 9 shows the frequency of CFSEpos cells recovered in tumor or spleen. Each bar shows average of five synchronously analyzed tumors or spleens±s.d. in a single experiment for each Step 1 condition or for background staining ("No cells given"). t-test for "Flt3L+IL6" vs "Flt3L+GMCSF" or "Flt3L+IL6+GMCSF" conditioning, p1<0.001. Results in FIG. 9 are representative of three separate experiments;

FIG. 11 shows the distribution of CD11c$^{pos}$ cells by B220 expression (B220$^{neg}$ myeloid DC phenotype vs B220$^{pos}$ plasmacytoid DC phenotype), tabulated at the end of Step 1 culture;

FIG. 12 shows the distribution of Gr1$^{pos}$ cells between MHC Class II$^{neg}$ cells vs MHC Class II$^{low}$ cells, tabulated from the same experiment at the end of Step 2 culture;

FIG. 13A shows photographs of individual T cell cultures after 6 day stimulation with DCs (DC prior conditioning treatments shown in labels) or with anti-CD3. Cultures shown also received exogenous IL2, IL7 and IL15. FIG. 13B is a graph tabulating T cell expansions. The fold-expansion from day 0 to day 12 for individual T cell cultures in FIG. 13A, following initial co-culture with DCs (labels indicate earlier DC conditioning treatments) or with anti-CD3. As distinguished in the legend, the displayed T cell expansions were performed either with no added cytokine, added rIL2 only (24 I.U./ml beginning day 2 of T cell culture), or IL2+1L7+IL15 (50 ng IL7, 5 ng IL15). This is representative of 3 experiments;

FIG. 14 is a graph showing DCs and T cells from MCA-203 bearing mice that were co-cultured. After 12 day culture expansion, T cells were harvested for therapy. Syngeneic mice bearing 10 day established subcutaneous MCA-203 tumors were treated with adjunct nonmyeloablative total body irradiation (500 cGy), and optionally received 10 million culture-expanded T cells, 5 mice per group. Cure rates were 0/5 (A, 500 cGy only) or 5/5 (B, 500 cGy, then 10 million "Flt3L+IL6" DC driven T cells). Treatment outcome A vs B p1<0.008This is representative of 2 experiments;

FIG. 17 is a graphic rendering of pSTAT3 vs. pSTAT5 staining at the end of Step 1 cultures. Each bar shows average fluorescence specificity index±s.d. of four side-by-side experimental runs for each conditioning regimen. Staining was significantly different for Flt3-L+IL-6 vs. all other groups both for pSTAT3 (p1 range <0.004 to <0.007) and for pSTAT5 (p1 range <0.001 to <0.011). No significant differences in pSTAT3 or pSTAT5 staining were observed among the GMCSF-containing groups (p1 range <0.190 to <1.0). Results in FIG.17 is a representative of three separate experiments, respectively;

FIG. 18 shows ELISA comparisons of supernatants for IL-12p70 at end of Step 2 culture. BM was obtained from KO mice or from matched wildtype LMs, placed in standard Step 1 cultures with Flt3-L+IL-6, Flt3-L+IL-6+GMCSF, or GMCSF alone as conditioning agents, then placed in 48 hr Step 2 cultures with GMCSF+IL-4 with CpG+LPS included during the final 18 hours. Culture failure was observed during Step 1 culture only when STAT3KO BM was conditioned with Flt3-L+IL-6. Data are presented as mean±s.d. of 3 replicates and are representative of three (STAT5KO vs LM) or two (STAT3KO vs LM) independently performed experiments;

In FIG. 29, Flt3-L stimulates pan-differentiation of CD34$^{pos}$ common myeloid and common lymphocyte precursors into CD11$^{pos}$ committed DC precursors via a STAT3-dependent process. This is markedly potentiated by IL-6, but is dominantly suppressed by Step 1 exposure to GMCSF, due to inhibition of STAT3 activation and concomitant STAT5 activation. Such Step 1 GMCSF exposure instead favors differentiation of CD34$^{pos}$ common myeloid precursors into granulocyte/monocyte progenitors (rather than committed DC precursors). The granulocyte/monocyte progenitors achieve subsequent multilineage differentiation, including STAT5-dependent differentiation into conventional DCs and macrophages, and STAT5-independent differentiation into neutrophils. Phenotypically conventional DCs generated by STAT3- vs. STAT5-dependent pathways differ in many critical characteristics. It should be emphasized that although Step 1 exposure to GMCSF blocks STAT3-dependent DC differentiation, Step 2 exposure of committed DC precursors to GMCSF may instead promote maturation and DC1-polarization, again by stimulating STAT5 and inhibiting STAT3;

DETAILED DESCRIPTION

The present invention relates to a method of generating a dendritic cell (DC) population from progenitor cells, and more particularly to a method of generating a population of DC precursors from $CD34^{pos}$ progenitor cells. The present invention is based on the discovery that conditioning of progenitor cells with Flt3 ligand (Flt3-L) and interleukin-6 (IL-6), in the absence of granulocyte-macrophage colony-stimulating factor (GMCSF), generates a large number of DC precursors having a unique cell surface marker phenotype $B220^{pos}/CD11c^{neg}/MHC$ Class $II^{neg}$. Conditioning with Flt3-L and IL-6, in the absence of GMCSF, induces nearly uniform and maximal $CD34^{pos}$ cell responsiveness to conventional DC maturational stimuli; primes DC precursors for a degree of spontaneous DC maturation even when signaling guidance is minimal; and transforms contact with tumor into a stimulus similar in impact to a single toll-like receptor (TLR) agonist both in vitro and in vivo. Based on this discovery, the present invention provides progenitor cell-derived DC precursors, methods for producing the DC precursors, and therapeutic uses thereof.

Figure 1:
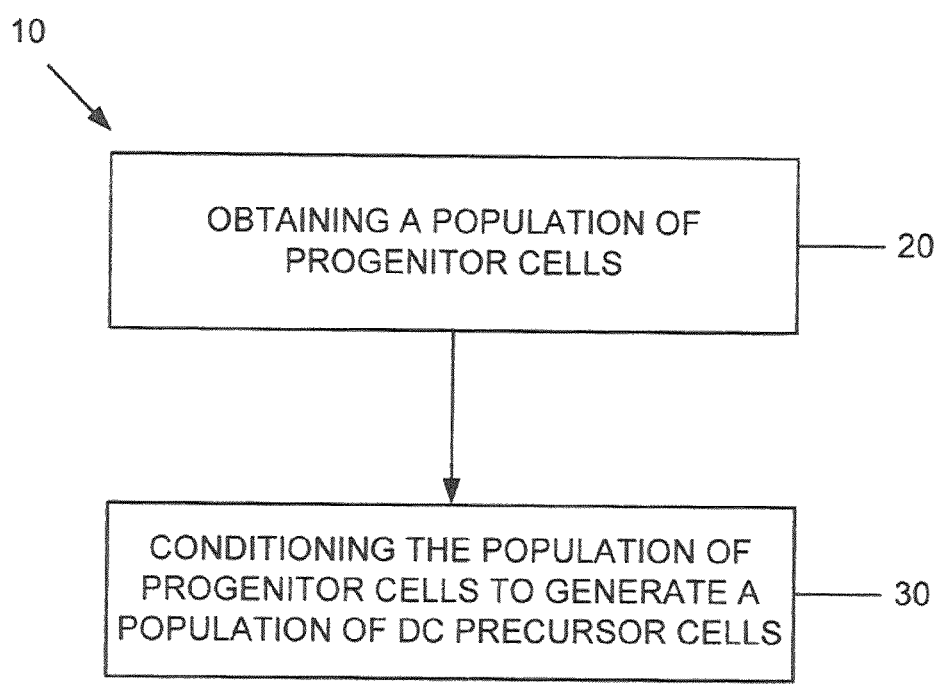
FIG. 1 is a flowchart illustrating a method for generating a population of dendritic cell (DC) precursors in accordance with the present invention.
Figure 2:
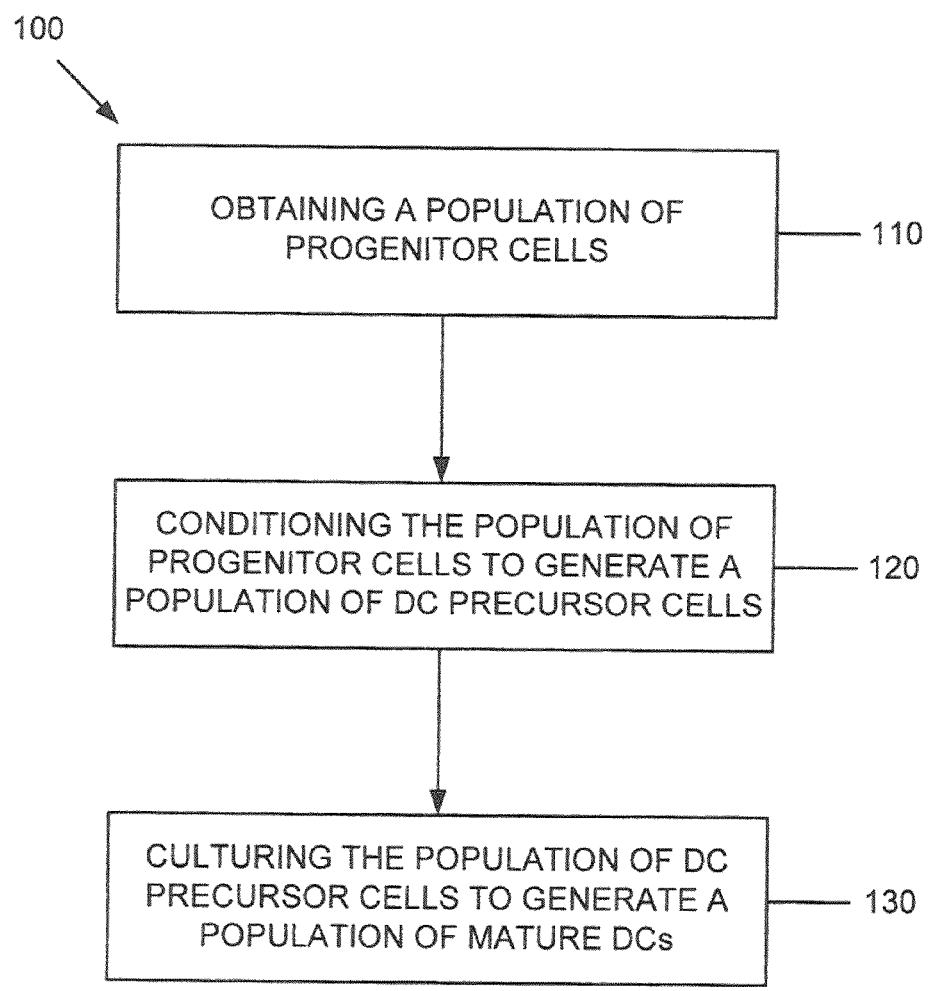
FIG. 2 is a flowchart illustrating a method for generating a population of mature DCs in accordance with the present invention.

FIG. 1 is a flow diagram illustrating a method 10 for generating a population of DC precursors in accordance with an aspect of the invention. In the method 10, a population of progenitor cells is obtained. The term "progenitor cell" as used herein refers to a cell that is capable of differentiating into any number and type of final, differentiated cell. The progenitor cell may be unipotent, oligopotent, multipotent, totipotent or pluripotent, such as unipotent, oligopotent, multipotent, totipotent or pluripotent progenitor and stem cells that are capable of differentiating into DC precursors. A totipotent cell typically has the capacity to develop into any cell type. A totipotent cell is usually embryonic in origin. A pluripotent cell is typically a cell in a cell line capable of differentiating into several different, final differentiated cell types.

In one aspect of the present invention, a progenitor cell can include a hematopoietic stem cell. Hematopoietic stem cells are clonogenic, self-renewing pluripotent cells capable of ultimately differentiating into all cell types of the hematopoietic system.

In another aspect of the present invention, a progenitor cell can include a myeloid progenitor cell. "Myeloid progenitor cell" refers to a multipotent or unipotent progenitor cell capable of ultimately developing into any of the terminally differentiated cells of the myeloid lineage, but which do not typically differentiate into cells of the lymphoid lineage. Hence, "myeloid progenitor cell" refers to any progenitor cell in the myeloid lineage. Committed progenitor cells of the myeloid lineage encompass unipotent erythroid progenitor, megakaryocyte progenitor, granulocyte progenitor, and macrophage progenitor cells. Different cell populations of myeloid progenitor cells are distinguishable from other cells by their differentiation potential, and the presence of a characteristic set of cell markers.

In another aspect of the present invention, a progenitor cell can include a common myeloid progenitor cell. "Common myeloid progenitor cell" refers to a cell characterized by its capacity to give rise to granulocyte/monocyte progenitor cells and megakaryocyte/erythroid progenitor cells. These progenitor cells have limited or no self-renewing capacity, but are capable of giving rise to myeloid dendritic, myeloid erythroid, erythroid, megakaryocytes, granulocyte/macrophage, granulocyte, and macrophage cells.

In another aspect of the present invention, a progenitor cell can include a lymphoid progenitor cell. "Lymphoid progenitor cell" refers to an oligopotent or unipotent progenitor cell capable of ultimately developing into any of the terminally differentiated cells of the lymphoid lineage, such as T cell, B cell, NK cell, or lymphoid dendritic cells, but which do not typically differentiate into cells of the myeloid lineage. As with cells of the myeloid lineage, different cell populations of lymphoid progenitors are distinguishable from other cells by their differentiation potential, and the presence of a characteristic set of cell markers.

In another aspect of the present invention, a progenitor cell can include a common lymphoid progenitor cell. "Common lymphoid progenitor cell" refers to an oligopotent cell characterized by its capacity to give rise to B-cell progenitors, T-cell progenitors, NK cells, and dendritic cells. These progenitor cells have little or no self-renewing capacity, but are capable of giving rise to T lymphocytes, B lymphocytes, NK cells, and lymphoid dendritic cells.

"Obtaining" progenitor cells means enriching, selecting and/or isolating cells from a population of cells, such as a mixed population of cells. A progenitor cell culture does not have to be comprised of solely or substantially progenitor cells, but can be a homologous population of progenitor cells. The present invention extends to heterogeneous mixtures of cells provided the mixtures comprise progenitor cells and, in particular, cells capable of generating DC precursors.

Reference to a "population" includes reference to an isolated culture comprising a homogenous, a substantially homogenous, or a heterogeneous culture of cells. Generally, a "population" may also be regarded as an "isolated" culture of cells.

Progenitor cells may be derived from various biological sources. Biological sources may include, for example, both human and non-human organisms. Non-human organisms contemplated by the present invention include primates, livestock animals (e.g., sheep, pigs, cows, horses, donkeys), laboratory test animals (e.g., mice, hamsters, rabbits, rats, guinea pigs), domestic companion animals (e.g., dogs, cats), birds (e.g., chicken, geese, ducks, and other poultry birds, game birds, emus, ostriches), captive wild or tamed animals (e.g., foxes, kangaroos, dingoes), reptiles and fish.

Progenitor cells may be obtained from a single subject, that is, the cells may be autologous, or from a plurality of subjects. "Autologous" refers to deriving from or originating in the same subject or patient. For example, an autologous cell transplant refers to the harvesting and reinfusion of a subject's own cells. Exclusive or supplemental use of autologous cells may eliminate or reduce many adverse effects of administration of the cells back to the host (i.e., graft-versus-host reaction). When progenitor cells are obtained from a plurality of donors, their relationship may be syngeneic, allogeneic or xenogeneic. "Allogeneic" refers to deriving from, origininating in, or being members of the same species, where the members are genetically related or genetically unrelated but genetically similar. An allogeneic cell transplant, for example, refers to transfer of cells from a donor to recipient, where the recipient is the same species as the donor.

Progenitor cells can be derived from various tissue types. Hematopoietic stem cells, for example, can be obtained from a variety of tissue types, including lymphoid and non-lymphoid tissues. Examples of suitable tissue types include any one or combination of bone marrow, peripheral blood, peripheral blood mononuclear cells, stem cells, monocytes, amniotic fluid, chorionic villus, cord and/or blood.

Progenitor cells of the present invention can be separated or isolated using a variety of known laboratory techniques. In one aspect of the present invention, progenitor cells capable of generating DC precursors may be isolated through cell culture. More particularly, a tissue sample may be collected from a subject and then propagated under desirable cell culture conditions (i.e., using particular cytokines and/or growth factors) known to promote survival and growth of progenitor cells. For example, bone marrow cells may be obtained from a subject and then seeded at about 0.5 million cells/ml in complete culture medium (RPMI 1640 with 10% fetal calf serum (FCS), standard nutritional supplements and antibiotics), placed in 75 cm$^2$ flasks, and then cultured so as to promote growth and selection of cells (i.e., DC precursors).

In another aspect of the present invention, a characteristic cell marker or set of cell markers may be used to identify and separate cells. Hematopoietic stem cells, for example, typically express the characteristic cell markers CD34 and/or CD90. As discussed in further detail below, a variety of selection techniques are known in the art for identifying and separating cells, such as CD34$^{pos}$ progenitor cells, from a population of cells. It should be understood that such techniques may also be used in combination with cell culture-based isolation methods.

Both negative and positive selection methods known in the art may be used to obtain a substantially pure population of progenitor cells. One technique, known as fluorescence activated cell sorting (FACS) or flow cytometry, may be used to sort and analyze different cell populations. Cells having the cellular marker(s) specific for progenitor cells may be tagged with an antibody, or typically a mixture of antibodies, that bind the cellular markers. Each antibody directed to a different marker may be conjugated to a detectable molecule, such as a fluorescent dye, that can be distinguished from other fluorescent dyes coupled to other antibodies. A stream of tagged or "stained" cells may be passed through a light source, which excites the fluorochrome, and the emission spectrum from the cells may then be detected to determine the presence of a particular labeled antibody. By concurrent detection of different fluorochromes, cells displaying different sets of cell markers may be identified and isolated from other cells in a cell population. Other FACS parameters, including, for example, side scatter, forward scatter, and vital dye staining (e.g., with propidium iodide) may allow selection of cells based on size and viability.

Another method of isolating progenitor cells uses a solid or insoluble substrate to which antibodies or ligands that interact with specific cell surface markers are bound. In such immunoadsorption techniques, cells may be contacted with the substrate (e.g., a column of beads, flasks, magnetic particles) containing the antibodies to remove any unbound cells. Suitable substrates include, for example, plastic, cellulose, dextran, polyacrylamide, agarose, and others known in the art (e.g., Pharmacia Sepharose 6MB macrobeads). When a solid substrate comprising magnetic or paramagnetic beads is used, cells bound to the beads can be readily isolated by a magnetic separator. Immunoadsorption techniques can be scaled up to deal directly with a large numbers of cells.

Affinity chromatographic cell separations typically involve passing a suspension of cells over a support bearing a selective ligand immobilized to its surface. The ligand interacts with its specific target molecule on the cell and is captured on the matrix. The bound cell is released by the addition of an elution agent to the running buffer of the column and the free cell is washed through the column and harvested as a homogeneous population. As apparent to the skilled artisan, adsorption techniques are not limited to those employing specific antibodies, and may use nonspecific adsorption. For example, adsorption to silica is a simple procedure for removing phagocytes from cell preparations.

FACS and most batch wise immunoadsorption techniques can be adapted to both positive and negative selection procedures (see, e.g., U.S. Pat. No. 5,877,299). In positive selection, desired cells are labeled with antibodies and removed away from the remaining unlabeled/unwanted cells. In negative selection, unwanted cells are labeled and removed. Another type of negative selection that can be employed is use of antibody/complement treatment or immunotoxins to remove unwanted cells.

The purification of cells may also include combinations of the methods described above. A typical combination may comprise an initial procedure that is effective in removing the bulk of unwanted cells and cellular material by, for example, leukapharesis. A second step may include isolation of cells expressing a cellular marker common to the progenitor cell population by immunoadsorption on antibodies bound to a substrate. For example, magnetic beads containing anti-CD34 antibodies can bind and capture progenitor cells that commonly express the CD34 antigen. An additional step providing higher resolution of different cell types, such as FACS sorting with antibodies to a set of specific cellular markers, can be used to obtain substantially pure populations of the desired cells. Another combination may involve an initial separation using magnetic beads bound with anti-CD34 antibodies followed by an additional round of purification with FACS.

After appropriately separating progenitor cells, cells can be frozen in a controlled rate freezer (e.g., Cryo-Med, Mt. Clemens, Mich.) and stored in the vapor phase of liquid nitrogen. Ten percent dimethylsulfoxide can be used as a cryoprotectant. After all collections from a donor have been made, the progenitor cells may be thawed and pooled as needed.

After obtaining the population of progenitor cells, at 30, the population of progenitor cells is conditioned in a culture medium for a time and under conditions sufficient to allow the progenitor cells to differentiate into a population of DC precursors having a characteristic cell surface marker phenotype. More particularly, a population of progenitor cells (e.g., CD34$^{pos}$ progenitor cells) is conditioned in a culture medium for a time and under conditions sufficient to allow the progenitor cells to differentiate into a population of DC precursor cells having a cell surface marker phenotype B220$^{pos}$/CD11c$^{neg}$/MHC Class II$^{neg}$.

The culture medium in which the cell are conditioned includes at least one cytokine and/or growth factor that is free of GMCSF to generate a population of DC precursors having a characteristic cell surface marker phenotype (e.g., cell surface marker phenotype B220$^{pos}$/CD11c$^{neg}$/MHC Class II$^{neg}$). In an aspect of the invention, the cell culture medium can contain Flt3-L and IL-6 in the absence of GMCSF. Additionally or optionally, the culture medium can include Flt3-L, IL-6 and SCF and also be free of GMCSF. By conditioning the cells in a culture medium including at least one cytokine and/or growth factor that is free of GMCSF, the progenitor cells differentiate into a DC precursor having a characteristic cell surface marker phenotype B220$^{pos}$/CD11c$^{neg}$/MHC Class II$^{neg}$ or the cell surface marker phenotype B220$^{pos}$/CD11c$^{neg}$/MHC Class II$^{neg}$/CD45RA$^{pos}$. Conditioning of progenitor cells yields a significant expansion of DC precursor cells. Expanded DC precursors are capable of rapid DC1-type polarization and require fewer DC maturational signals.

Progenitor cells can be conditioned for a time appropriate to generate a population of DC precursors having the characteristic cell surface marker phenotype. For example, progenitor cells can be conditioned for about 2 to about 10 days. More particularly, progenitor cells can be conditioned for about 6 to about 7 days to generate a population of DC precursors having the cell surface marker phenotype $B220^{pos}/CD11c^{neg}/$MHC Class $II^{neg}$.

Progenitor cells may be conditioned using appropriate culture conditions capable of promoting DC precursor generation. For example, progenitor cells can be conditioned in a culture medium including at least one cytokine and/or growth factor that is free of GMCSF. As used herein, "cytokine" refers to compounds or compositions that in the natural state are made by cells and affect physiological states of the cells that produce the cytokine (i.e., autocrine factors) or other cells. "Cytokine" also encompasses any compounds or compositions made by recombinant or synthetic processes, where the products of those processes have identical or similar structure and biological activity as the naturally occurring forms. For example, recombinant human (rh) and/or recombinant murine (rm) cytokines may be used.

The phrase "growth factor" as used herein refers to a compound or composition that in the natural state affects cell proliferation, cell survival, and/or differentiation. A growth factor, while having the indicated effect on the cell, may also affect other physiological processes, such as secretion, adhesion, response to external stimuli, and the like. Although many growth factors are made by cells, "growth factor" as used herein also encompasses any compound or composition made by recombinant or synthetic processes, where the product of those processes have identical or similar structure and biological activity as the naturally occurring growth factor. For example, recombinant human and/or recombinant murine growth factors may be used.

Additional cytokines and/or growth factors may be included in the culture medium so long as a population of DC precursors is generated by the addition thereof. Examples of cytokines and growth factors which may be included in the culture medium include, without limitation, IL-3, IL-4, TNF-α, TNF-β, LT-β, IL-2, IL-7, IL-9, IL-15, IL-13, IL-5, IL-1α, IL-1β, IFN-γ, IL-10, IL-17, IL-16, IL-18, HGF, IL-11, MSP, FasL, TRAIL, TRANCE, TWEAK, CD27L, CD30L, CD40L, APRIL, TALL-1, 4-1BBL, OX40L, GITRL, IGF-1, IGF-II, MSP, FGF-α, FGF-β, FGF-3-19, NGF, BDNF, NTs, Tpo, Epo, Ang1-4, PDGF-AA, PDGF-BB, VEGF-A, VEGF-B, VEGF-C, VEGF-D, PlGF, EGF, TGF-α, AR, BTC, HRGs, HG-EGF, SMDF, OB, CT-1, CNTF, OSM, MK, PTN, or their functional, recombinant, chemical equivalents, homologue, or combinations thereof.

Additionally, the culture medium may include other additives, such as growth media that allow for the survival and proliferation of the DC precursors. Examples of growth media include RPMI 1640, DMEM and α-MEM, with added amino acids and vitamins supplemented with an appropriate amount of serum or a defined set of hormones sufficient to promote proliferation of the DC precursors. Serum-free media supplemented with hormones is also suitable for culturing the DC precursors. Cells may be selected or adapted to grow in other serums and at different concentrations of serum. Growth media may also contain antibiotics, such as penicillin and gentamicin, to minimize bacteria infection of the cultures.

In another aspect of the present invention, the cell surface marker phenotype of cells, such as DC precursors, may be determined by marker phenotyping. Methods for determining cell surface marker phenotype (referred to as "marker phenotyping" herein) are well known in the art. "Marker phenotyping" refers to identification of markers or antigens on cells for determining their phenotype (e.g., differentiation state and/or cell type). This may be done by immunophenotyping, which uses antibodies that recognize antigens present on a cell. The antibodies may be monoclonal or polyclonal, but are generally chosen to have minimal crossreactivity with other cell markers. Cell markers can include cell surface molecules, also referred to in certain situations as cell differentiation (CD) markers. It is to be understood that certain CD or cell surface markers are unique to the animal species from which the cells are derived, while other cell markers will be common between species. These markers defining equivalent cell types between species are given the same marker identification even though there are species differences in structure (e.g., amino acid sequence).

One or a combination of cell surface markers may be used to identify the various DC populations of the present invention. These include, for example, the presence of large amounts of MHC Class II antigens and the absence of various lineage markers such as CD3 (T cell), CD14 (monocyte), CD19 (B cell), CD56 (NK cell) and CD66b (granulocyte). DCs also express a variety of adhesion molecules including CD11 a (LFA-1), CD11c, CD50 (ICAM-2), CD54 (ICAM-1), CD58 (LFA-3), and CD102 (ICAM-3). DCs also express costimulatory molecules including CD80 (B7.1), and CD86 (B7.2), which are up-regulated during DC activation. CD86 tends to be a marker of early DC maturation, while CD80 only appears in mature DC. Two additional markers of mature DCs in humans are CD83 and CMRF-44. CD83 also stains activated B cells, and CMRF-44 will also stain macrophages and monocytes. Numerous other suitable cell surface markers (e.g., PDCA, CD40, OX40L, CD1a, CD209, CR2, FCER2, FSCN1, CD127, CD90, CD10, CD123 and Lin2) are presently known to the skilled artisan, or will be identified and characterized in due course, and such makers will find advantageous use in the methods and compositions described herein.

In an example of the method, cell suspensions may be prepared from the bone marrow of a subject. Unfractionated cells may then be cultured at about 0.5 million cells/ml in 75 cm² flasks in standard culture medium consisting of RPMI 1640 (with about 10% heat deactivated FCS, about 0.1 mM non-essential amino acids, about 1 mM sodium pyruvate, about 2 mM L-glutamine, about 100 mg/ml streptomycin, about 100 U/ml penicillin, about 50 mg/ml gentamicin, about 0.5 mg/ml, and about $5 \times 10^5$ M 2-mercaptoethanol), hFlt3-L (about 25 ng/ml to about 300 ng/ml) and mIL-6 (about 25 ng/ml to about 100 ng/ml; about 100 ng/ml of rhIL-6 may also be used). Additionally, mSCF (about 25 ng/ml to about 100 ng/ml) may also be included in the culture medium. Cells may then be grown for about 6-7 days, harvested, counted, and then washed in PBS. After conditioning, the cells may exhibit the characteristic cell surface marker phenotype $B220^{pos}/CD11c^{neg}/MHC$ Class $II^{neg}$.

Alternatively, it should be understood that cells may be fractioned using FACS prior to culture. Using FACS, for example, $CD34^{pos}$ cells may be isolated from the bone marrow-derived cell population and grown for about 6-7 days in standard culture medium containing Flt3-L and IL-6 in the absence of GMCSF. The cells may then be harvested, counted, and then washed in PBS.

The absence of GMCSF in progenitor cell culture has pronounced effects on DC precursor formation and subsequent maturation. For example, a pronounced dichotomy was evident when comparing DC maturation potential in cells conditioned with GMCSF and cells conditioned with Flt3-L in the absence of GMCSF. Despite the proliferative synergy evident when GMCSF and Flt3-L were given together as conditioning agents (FIG. 5), the presence of GMCSF resulted in numeric expansion of cells with a significantly limited potential for DC maturation. Moreover, the presence of GMCSF in the culture medium during conditioning not only diminished the ability of DC precursor cells to effectively achieve DC1-type polarization, but also diminished the frequency of DC precursors.

Figure 3:
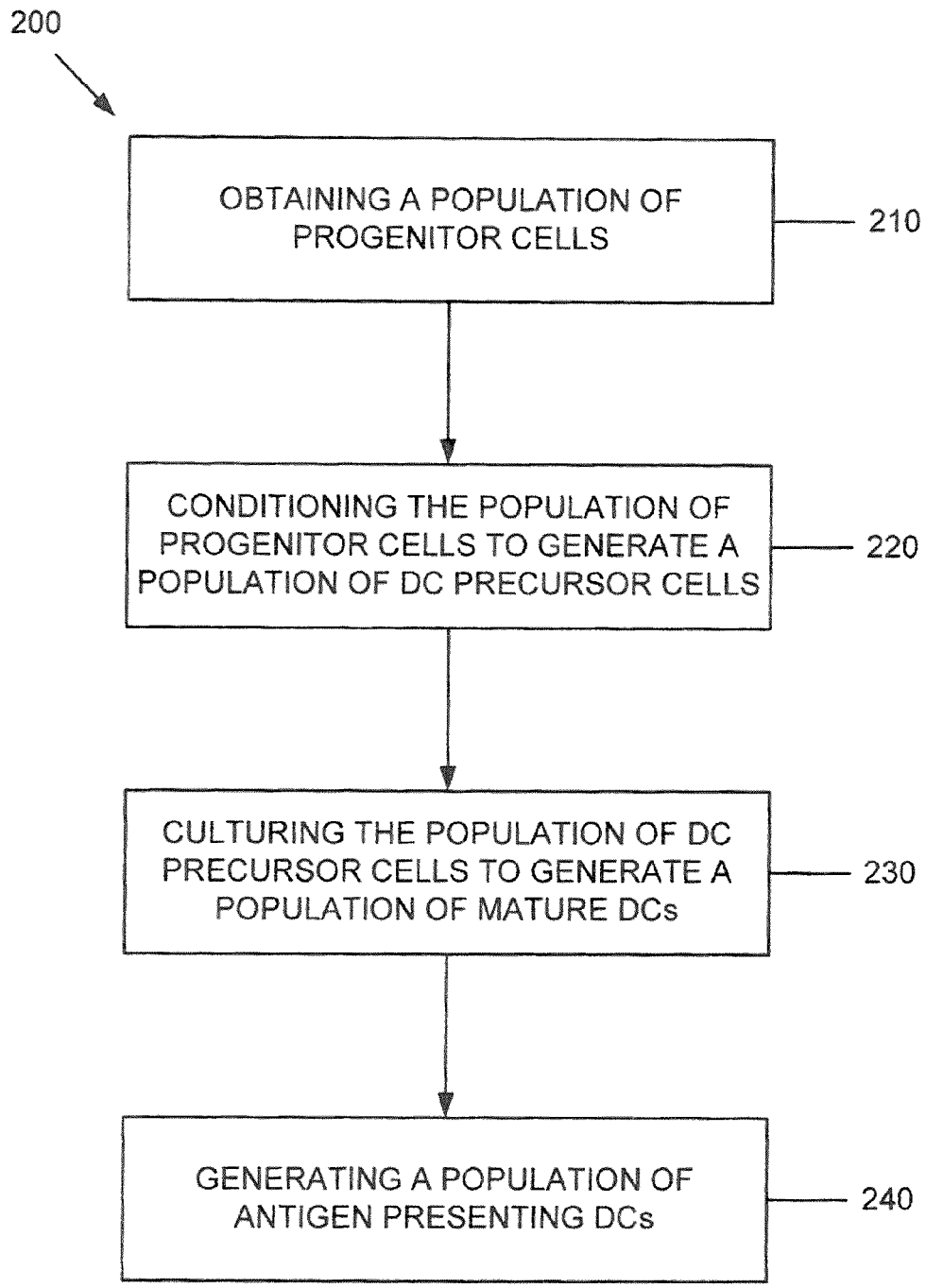
FIG. 3 is a flowchart illustrating a method for preparing a vaccine preparation in accordance with the present invention.

FIG. 3 illustrates a method 100 of generating a population of mature DCs in accordance with another aspect of the invention. In the method 100, at 110, a population of progenitor cells is obtained in a manner similar to the manner in which the progenitor cells are obtained in the method 10 described above. At 120, a population of DC precursors is generated having a characteristic cell surface marker phenotype in a manner similar to the manner in which the DC precursors are generated in the method 10. At 130, a mature DC population is generated from the DC precursors. The mature DC population may be generated by culturing the DC precursors in a culture medium that includes at least one agent capable of promoting maturation of the DC precursors into the mature DC population. Alternatively, the mature DC population may be generated when the DC precursors spontaneously mature into the mature DC population.

As used herein, "mature DC" refers to an antigen presenting cell existing in vivo, in vitro, ex vivo, or in a host or subject that is DC1-polarized (i.e., fully capable of promoting cell-mediated immunity). "Cell-mediated immunity" refers to an immune response that does not involve antibodies, but rather involves the activation of macrophages and NK cells, the production of antigen specific cytotoxic T-lymphocytes, and the release of various cytokines in response to an antigen.

DC precursors can be cultured for a period of time sufficient to generate a population of mature DCs. For example, the DC precursors may be cultured for about 1 to about 5 days, either in the presence or absence of at least one agent capable of promoting maturation of the DC precursors. In another example, the DC precursors may be cultured for about 2 to about 3 days, either in the presence or absence of at least one agent capable of promoting maturation of the DC precursor cells.

The agent capable of promoting maturation of DC precursors into a mature DC population can include a cytokine or growth factor. Examples of cytokines and growth factors capable of promoting maturation of the DC precursors into mature DCs include, without limitation, Flt3-L, SCF, IL-6, IL-3, IL-4, TNF-α, TNF-β, LT-β, IL-2, IL-7, IL-9, IL-15, IL-13, IL-5, IL-1α, IL-1β, IFN-γ, IL-10, IL-17, IL-16, IL-18, HGF, IL-11, MSP, FasL, TRAIL, TRANCE, TWEAK, CD27L, CD30L, CD40L, APRIL, TALL-1, 4-1BBL, OX40L, GITRL, IGF-1, IGF-II, MSP, FGF-α, FGF-β, FGF-3-19, NGF, BDNF, NTs, Tpo, Epo, Ang1-4, PDGF-AA, PDGF-BB, VEGF-A, VEGF-B, VEGF-C, VEGF-D, PlGF, EGF, TGF-α, AR, BTC, HRGs, HG-EGF, SMDF, OB, CT-1, CNTF, OSM, MK, PTN, or their functional, recombinant, chemical equivalents, homologue, or combinations thereof.

Additionally or optionally, the agent capable of promoting maturation of the DC precursors into the mature DC population can include a TLR agonist (e.g., CpG motifs, LPS, and/or combinations thereof), a CD40 ligand, a calcium ionophore, a tumor-derived immunosuppressive factor (e.g., IL-10, TGF-β, VEGF, PGE$_2$), a tumor cell, tumor cell lysate, and combinations thereof.

In an example of the method, progenitor cells can be respectively obtained and conditioned to generate a population of DC precursors having a characteristic cell surface marker phenotype. DC precursors may be cultured in standard culture medium consisting of RPMI 1640 (with about 10% heat deactivated FCS, about 0.1 mM non-essential amino acids, about 1 mM sodium pyruvate, about 2 mM L-glutamine, about 100 mg/ml streptomycin, about 100 U/ml penicillin, about 50 mg/ml gentamicin, about 0.5 mg/ml, and about $5\times10^5$ M 2-mercaptoethanol) and including at least one agent, such as rmIL-4 (about 10 ng/ml to about 25 ng/ml), capable of promoting DC precursor maturation. The population of DC precursors may be cultured for about 2-3 days in 24 well cluster plates, with about 4 million cells per well, in about 2 ml standard culture medium. Additional agents capable of promoting maturation, such as CpG (ODN 1826, about 5 μM) and LPS (about 50 ng/ml), can also be included in the culture medium. Immunosuppressive agents such as rmIL-10, rmVEGF, rhTGF-β1 and/or PGE$_2$ may also be added to the culture medium. Alternatively or additionally, particulate tumor cells, either viable unirradiated, viable irradiated (10,000 cGy), or killed freeze-thawed lysate may be added to the DC precursors to promote maturation of the DC precursors into mature DCs.

Mature DCs conditioned in the absence of GMCSF exhibit superior developmental characteristics. For example, the addition of GMCSF at Step 120 generates DCs which retain an immature phenotype, activate regulatory T cells, and promote tumor growth. Conversely, DC precursors conditioned with Flt3-L and IL-6, in the absence of GMCSF, were able to spontaneously mature into DC1-type polarized DCs in the absence of additional stimuli.

Mature DCs of the present invention also exhibit superior resistance to immunosuppressive factors and are able to mature in the presence of tumorogenic material. Unlike DCs conditioned with GMCSF, DCs conditioned with Flt3-L and IL-6 in the absence of GMCSF exhibited progressive resistance to PGE$_2$ inhibition. Additionally, after Flt3L+IL6 conditioning in the absence of GMCSF, post-proliferative contact with tumor materials actually accelerated DC maturation.

In another aspect of the present invention, the DC precursors, the mature DCs, and/or combinations thereof may be used to provide therapeutic treatments to a subject in need thereof. Additionally or optionally, particular mixtures of cytokines and/or growth factors may be used as therapeutic treatments. As used herein, the phrase "therapeutic treatment" refers to a treatment administered to a subject who displays symptoms or signs of pathology, disease, or disorder, in which treatment is administered to the subject for the purpose of diminishing or eliminating those signs or symptoms of pathology, disease or disorder.

FIG. 3 illustrates a method 200 for preparing a vaccine preparation that can be used for therapeutic treatment in accordance with an aspect of the invention. In the method 200, at 210, progenitor cells are obtained in a manner similar to the manner described in method 10. At 220, progenitor cells are conditioned in a manner similar to the manner in method 10 to generate DC precursors. At 230, the DC precursors are matured to generate a population of mature DCs in a manner similar to the manner in the method 100. At 240, a population of antigen-presenting DCs is formed from the population of mature DCs. Methods for presenting an antigen on the surface of a DC are known in the art and described in more detail below. The antigen-presenting DCs may be capable of activating a population of T cells (i.e., CD4$^{pos}$ and/or CD8$^{pos}$) occurring in vitro and/or in vivo.

The mature DCs of the present invention are highly effective antigen presenting cells capable of priming and stimulating T cell responses to a wide variety of antigens. Accordingly, the population of antigen presenting DCs may be useful for inducing an immune response in a subject against tumors as well as numerous bacterial and other pathogens. For example, the cells may be useful as a prophylactic and/or therapeutic method for treating diseases and disorders.

Pathogens and diseased cells, e.g., tumor, necrotic, or apoptotic cells, express a variety of antigens implicated in the cell-mediated immune response. T cells recognizing such epitopes are stimulated to proliferate in response to antigen presenting cells, i.e., DCs, which display an antigen on a MHC molecule. Examples of antigens include, for example, tumor derived antigens (e.g., prostate specific antigen); colon cancer antigens (e.g., CEA); breast cancer antigens (e.g., HER-2); leukemia antigens; melanoma antigens (e.g., MAGE-1, MART-1); antigens to lung, colorectal, brain, and pancreatic cancers; antigens to renal cell carcinoma, sarcomas, and neuroblatomas; viral antigens (e.g., hepatitis B core and surface antigens (HBVc, HBVs), hepatitis A, B or C antigens, Epstein-Barr virus antigens, CMV antigens, human immunodeficiency virus (HIV) antigens, herpes virus antigens, and human papilloma virus (HPV) antigens); bacterial and mycobacterial antigens (e.g., for TB, leprosy, or the like); other pathogen derived antigens (e.g., Malarial antigens from *Plasmodium* sp.); and other cellular antigens (e.g., tyrosinase, trp-1). Many other antigen types are known and available, and can be presented by the mature DCs of the present invention.

Proteins or peptide fragments which are differentially expressed in cancers, such as those associated with melanoma (e.g., MART-1, gp100, TRP-1, TRP-2 or tyrosinase) can be externally loaded onto or expressed in mature DCs for antigen presentation to T cells. Similarly, proteins associated with breast cancers (e.g., c-erb-2, bcl-1, bcl-2, and vasopressin related proteins) and other carcinomas (e.g., c-myc, int-2, hst-1, ras and p53 mutants, prostate-specific membrane antigen (PMSA) and papilloma virus protein L1) are suitable antigens for external loading or expression. Other tumor antigens for presentation include, but are not limited to, c-erb-β-2/HER2/neu, PEM MUC-1, Int-2, Hst, BRCA-1, BRCA-2, EGFR, CEA, p53, ras RK, Myc, Myb, OB-1, OB-2, BCR/ABL, GIP, GSP, RET, ROS, FIS, SRC, TRC, WTI, DCC, Nfi, FAP, MEN-1, and ERB-B11.

Antigens derived from pathogens, including viral, bacterial, intracellular and extracellular parasites are also suitable antigens for loading onto or expressing in mature DCs. Numerous viral proteins are suitable for presentation, including, for example, those of papilloma viruses, HIV (e.g., Gag and Env antigens) and hepatitis (e.g., HBs-Ag), among many others.

Antigens derived from bacterial agents are also suitable for display or presentation by mature DCs, including, for example, those derived from *chlamydia*, staphylococci, streptococci, pneumonococci, meningococci and conococci, *klebsiella*, proteus, *serratia, pseudomonas*, legionaella, diphtheria, *salmonella*, bacilli, cholera, tetanus, botulism, anthrax, plague, leptospirosis, rickettsial and Lyme disease bacteria.

Antigens of cellular parasites, such as Malaria, are also appropriate for loading onto or expressing in mature DCs. Malaria is caused by one of four species of *Plasmodium: P. falciparum, P. vivax, P. knowlesi* and *P. malariae*. Malaria is well studied, and a number of antigens suitable for cell mediated therapies are known.

In general, methods for peptide (or protein) loading for selected proteins and protein fragments onto DCs are known in the art and described in, for example, U.S. Patent Publication No. US2005/0002929 A1, which is herein incorporated by reference in its entirety. For example, electrofusion techniques may be used to load selected tumor proteins or protein fragments onto DCs. Electrofusing is a method of generating hybrid cells, and is typically performed by applying electric pulses to cells in suspension. By exposing cells to an alternating electric field, cells are brought close to each other in a process termed dielectrophoresis alignment. Subsequent higher voltage pulses causes cells to come into closer contact, and electropores are formed which reversibly permeabilize and mechanically break down cell membranes, resulting in cell fusion.

In some aspects of the present invention, the mature DCs can uptake whole proteins, process, and express peptide fragments of the protein on their respective surfaces. In other aspects, it may be desirable simply to wash endogenous peptide fragments off of the surface of the mature DCs (e.g., in a mildly acidic or detergent containing wash) and to then load peptide fragments onto the surface of the cells. Many such applications are known in the art. For example, Tsai et al. (1997) *J Immunol* 158:1796 describes the loading of GP-100 tumor associated antigens onto DCs. Alternatively, and for many applications, proteins or peptides comprising antigens can be expressed in the mature DCs or DC precursor cells using recombinant DNA technology.

In one example of the method, progenitor cells are obtained from a subject and then conditioned to generate DC precursors. DC precursors are then matured to generate a population of mature DCs. Antigen presenting cells are generated from the mature DCs. For example, mature DCs may be electrofused with tumor cells, such as prostate tumor cells, expressing prostate specific antigen (PSA). After successful electrofusion, the hybrid cells may present PSA on their cell surfaces. A population of PSA-presenting cells may then be re-introduced into the subject. In vivo, the PSA-presenting cells may stimulate the subject's cell-mediated immune response to effectively reduce or eliminate the prostate tumor cells.

Figure 4:
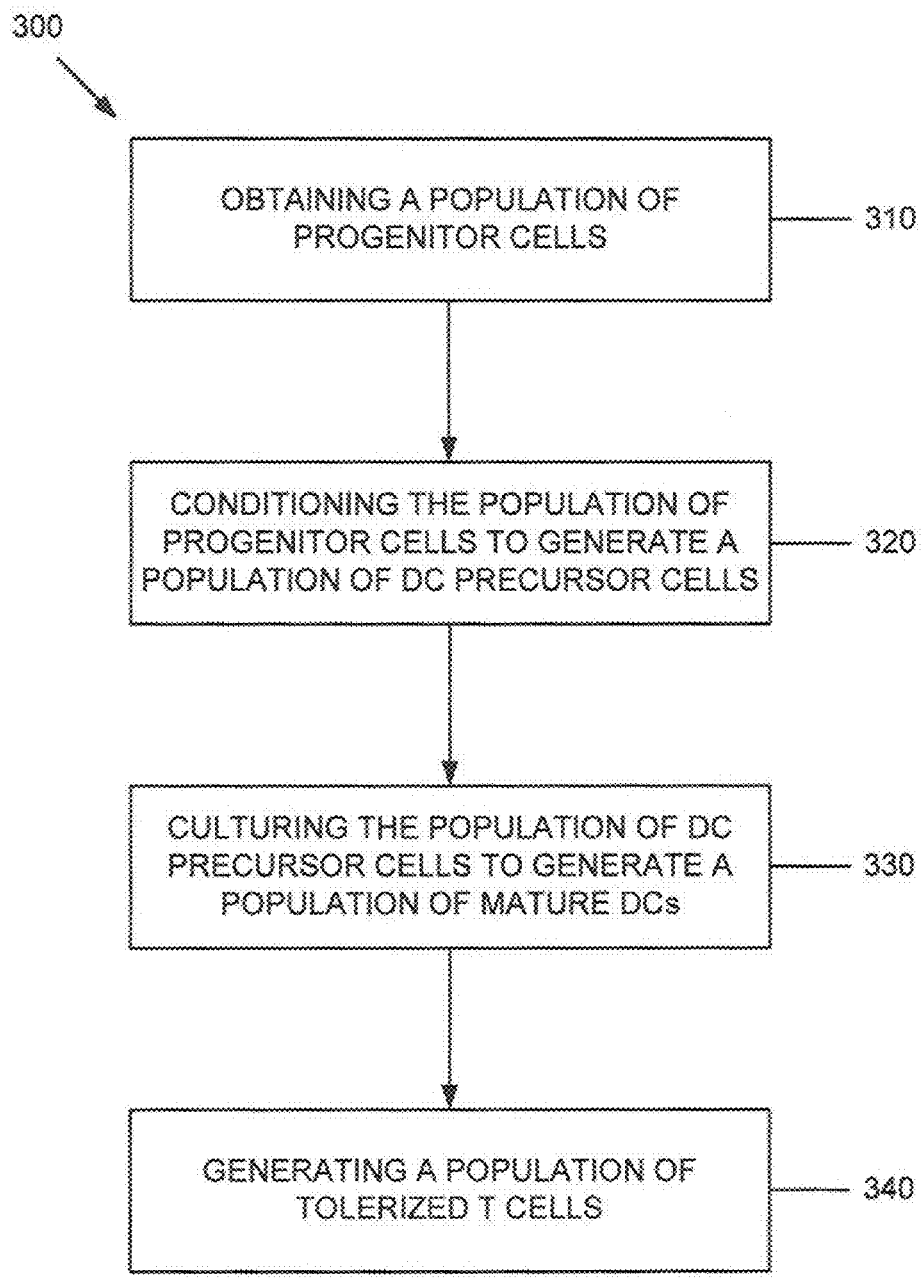
FIG. 4 is a flowchart illustrating a method for adoptive immunotherapy in accordance with the present invention.

FIG. 4 illustrates a method 300 for generating tolerized T cells useful in adoptive immunotherapy in accordance with an aspect of the invention. In the method 300, at 310 and 320, respectively, progenitor cells are obtained and conditioned to generate a population of DC precursors in a manner similar to the method 10. At 330, a mature DC population is generated in a manner similar to the method 100. At 340, T cells which have been sensitized to a particular antigen (e.g., T cells harvested from tumor-draining lymph nodes; referred to as "tolerized T cells" herein), are co-cultured with a population of mature DCs. As used herein, "tolerized T cells" refers to T cells which have been induced into an anergic state in which the T cells do not proliferate in response to subsequent antigen stimulation. Co-culture of mature DCs with tolerized T cells effectively reverses the tolerance of the T cells so that renewed T cell sensitization and production may occur upon delivery of the T cells to a subject.

Adoptive immunotherapy is the treatment of disease using cells of the immune system, e.g., T cells that have been activated or expanded ex vivo. Such modified cells are typically derived from a subject and used to supplement, enhance, replace or otherwise modify the subject's own inadequate or inappropriate immune response. Antigen-pulsed DCs, for example, may be used ex vivo to generate large numbers of autologous antigen-specific T cells for re-infusion into a subject. As noted above, mature DCs may alternatively be used ex vivo to generate large numbers of autologous antigen-specific T cells for re-infusion into a subject. Once infused into a subject, the T cells may attack and clear infected cells and thereby cure the disease.

In an example of the method, progenitor cells are obtained and conditioned to generate a population of DC precursors. DC precursors generated are then cultured in 1% non heat-deactivated serum (i.e., other than FCS), during which time the DC precursor cells are exposed to viable irradiated tumor cells and, optionally, exposed to CpG and/or LPS. Simultaneous with DC culture harvest, T cells are freshly harvested from the tumor-draining lymph nodes of a subject having a tumor. The T cells are cultured with immobilized anti-CD3 and/or DC precursors. The combined cells may then be cultured for a period of time (e.g., about 1 to 15 days) to reverse T cell tolerance. After the period of time, the T cells may be reintroduced into the subject where they may proliferate and attack the subject's tumor cells.

Figure 8:
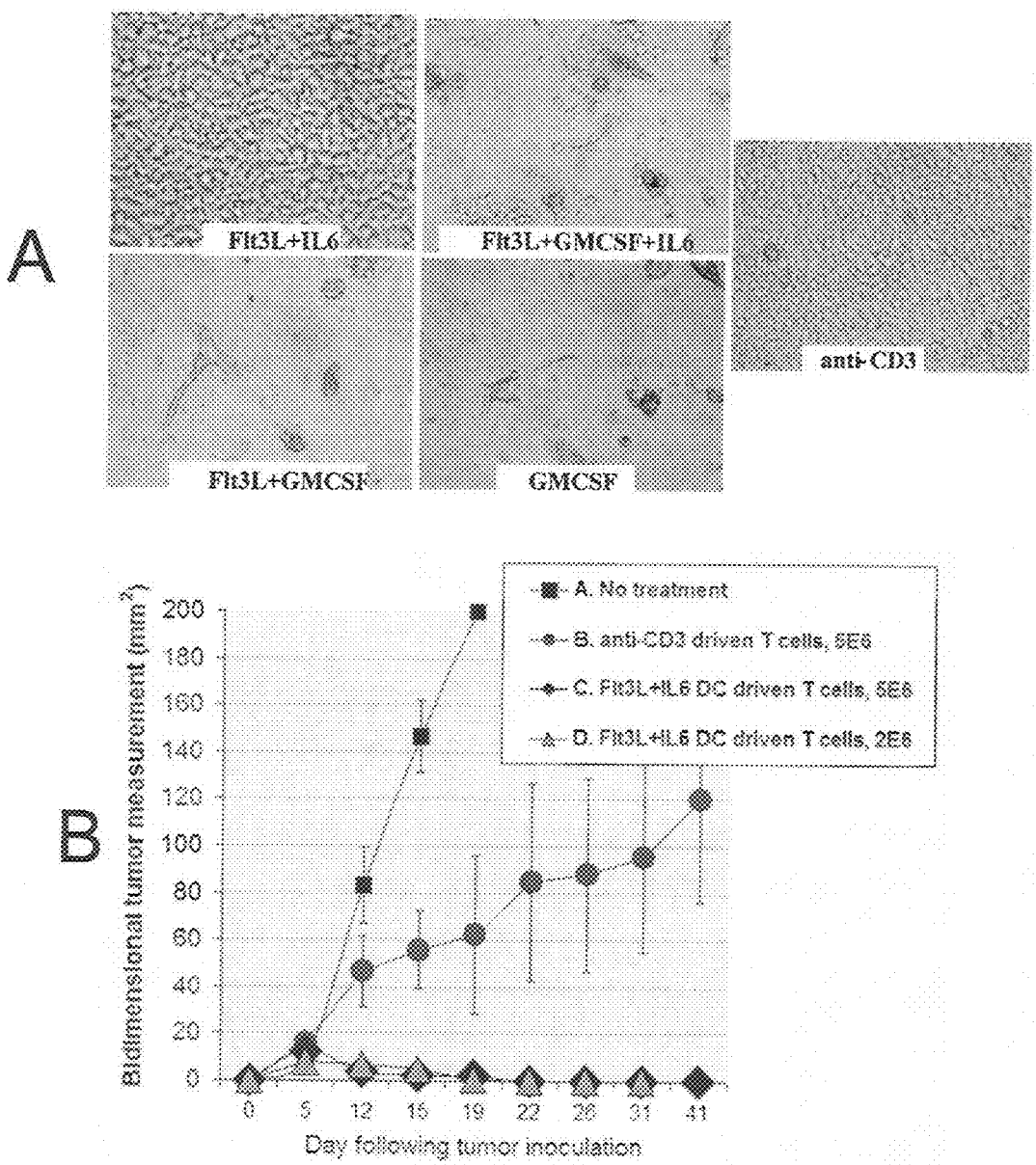
FIGS. 8A-B show the impact of initial Step 1 DC conditioning treatments upon later T cell cultures. Step 2 DC cultures were performed in rGMCSF and rIL-4 with irradiated MCA-203 cells added at 24 hr and CpG+LPS added at 44 hr. Four hours later, DCs were harvested for co-culture with L-selectin$^{low}$ T cells freshly harvested from MCA-203 tumor-bearing mice. T cells were co-cultured with DCs at an 8:1 ratio or were activated with immobilized anti-CD3.

When co-cultured with tolerized T cells, the DCs of the present invention may provide a superior means for promoting adoptive immunotherapy. For example, DCs conditioned with GMCSF and then co-cultured with tolerized T cells were ineffective for propagating the T cells, led to death of the T cells within several days of co-culture, and could not be rescued by addition of IL-2, IL-7 and/or IL-15. In fact, conditioning treatments usually proved lethal whenever GMCSF was present during the conditioning phase, even if Flt3-L or Flt3-L and IL-6 were also present. Conversely, T cell cultures driven by DCs conditioned with Flt3-L and IL-6 displayed superior outgrowth of both $CD4^{pos}$ and $CD8^{pos}$ tumor-specific T cells, and were also highly potent when administered in vivo as adoptive therapy (FIGS. 8B and 13B).

In another aspect of the present invention, the immune response of a subject may be up-regulated by administering an effective amount of a mixture including Flt3-L and IL-6 and being free of GMCSF. Additionally or optionally, the mixture may include Flt3-L, IL-6 and SCF and be free of GMCSF. Administering to a subject a mixture comprising Flt3-L and IL-6, in the absence of GMCSF, for example, may facilitate generation of an in vivo population of DC precursors. Either spontaneously or by concurrent or subsequent addition of at least one agent capable of promoting maturation of the DC precursors, the DC precursors may mature into a population of mature DCs fully capable of promoting cell-mediated immunity. These mature DCs may in turn stimulate new T cell production and sensitization.

As used herein, an "effective amount" means a dosage or amount sufficient to produce a desired result. The desired result may comprise an objective or subjective improvement it the recipient of the dosage or amount. Additionally, "mixture" means a composition suitable for pharmaceutical use in a subject, including an animal or human. A mixture generally comprises an effective amount of an active agent and a pharmaceutically acceptable carrier.

In another aspect of the present invention, the mixture may further include one or more cytokine and/or growth factor selected from the group consisting of IL-3, IL-4, TNF-α, TNF-β, LT-β, IL-2, IL-7, IL-9, IL-15, IL-13, IL-5, IL-1α, IL-1β, IFN-γ, IL-10, IL-17, IL-16, IL-18, HGF, IL-11, MSP, FasL, TRAIL, TRANCE, TWEAK, CD27L, CD30L, CD40L, APRIL, TALL-1, 4-1BBL, OX40L, GITRL, IGF-1, IGF-II, MSP, FGF-α, FGF-β, FGF-3-19, NGF, BDNF, NTs, Tpo, Epo, Ang1-4, PDGF-AA, PDGF-BB, VEGF-A, VEGF-B, VEGF-C, VEGF-D, PlGF, EGF, TGF-α, AR, BTC, HRGs, HG-EGF, SMDF, OB, CT-1, CNTF, OSM, MK, PTN, or their functional, recombinant, chemical equivalents, homologue, or combinations thereof.

The immune response of a subject may be up-regulated to treat any one or combination of known diseases, disorders, or conditions. For instance, the immune response of an immunocompromised subject may be up-regulated. Alternatively, a subject's immune response may be up-regulated to prevent, inhibit or reduce the presence of cancer.

The cancers contemplated by the present invention, against which the immune response is induced, or which is to be prevented, inhibited, or reduced in presence, may include but are not limited to melanoma, non-Hodgkin's lymphoma, Hodgkin's disease, leukemia, plasmocytoma, sarcoma, glioma, thymoma, breast cancer, prostate cancer, colo-rectal cancer, kidney cancer, renal cell carcinoma, pancreatic cancer, nasopharyngeal carcinoma, esophageal cancer, brain cancer, lung cancer, ovarian cancer, cervical cancer, multiple myeloma, heptocellular carcinoma, acute lymphoblastic leukemia, acute myelogenous leukemia, chronic myelogenous leukemia, large granular lymphocyte leukemia, and chronic lymphocytic leukemia.

The mixture of the present invention can also be used to restore immune responsiveness in immunocompromised subjects (e.g., subjects who have been treated with chemotherapy, cytotoxic agents, or any immunosuppressive agent known to those of skill in the art). Additionally, the mixture of the present invention can be used to treat (i.e., restore immune responsiveness) subjects who have undergone hematopoeitic stem cell transplantation or who have received cord blood, allogeneic, autologous, or xenogeneic cell transplants.

The mixture of the present invention may also be used to induce or enhance responsiveness to pathogenic agents, such as viruses, bacteria, parasites and fungi. More particularly, pathogenic agents can include viruses (e.g., single-stranded RNA viruses, single-stranded DNA viruses, HIV, hepatitis A, B, and C virus, herpes simplex virus, cytomegalovirus, Epstein-Ban virus, and HPV), parasites (e.g., protozoan and metazoan pathogens such as *Plasmodia* species, *Leishmania* species, *Schistosoma* species, and *Trypanosoma* species), bacteria (e.g., mycobacteria, in particular, *M. tuberculosis, salmonella*, streptococci, *E. coli*, and staphylococci), fungi (e.g., *Candida* and *Aspergillus* species), *Pneumocystis carinii*, and prions (e.g., kuru, Creutzfeldt-Jakob disease, Gerstmann-Straussler-Scheinker disease, and fatal familial insomnia).

In another aspect of the present invention, the immune response of a subject may be down-regulated by administering to the subject an effective amount of a mixture comprising Flt3-L and GMCSF. Administering Flt3-L and GMCSF to a subject, for example, may decrease the number and/or potency of in vivo T cells normally available to participate in the immune response. Such an effect may be desirable where an overabundance and/or hyperactivity of T cells are the source of, or contribute to, the subject's disease or condition.

Additionally or optionally, the mixture can include one or more cytokine and/or growth factor selected from the group consisting of SCF, IL-3, IL-4, IL-6, GCSF, TNF-α, TNF-β, LT-β, IL-2, IL-7, IL-9, IL-15, IL-13, IL-5, IL-1α, IL-1β, IFN-γ, IL-10, IL-17, IL-16, IL-18, HGF, IL-11, MSP, FasL, TRAIL, TRANCE, TWEAK, CD27L, CD30L, CD40L, APRIL, TALL-1, 4-1BBL, OX40L, GITRL, IGF-1, IGF-II, MSP, FGF-α, FGF-β, FGF-3-19, NGF, BDNF, NTs, Tpo, Epo, Ang1-4, PDGF-AA, PDGF-BB, VEGF-A, VEGF-B, VEGF-C, VEGF-D, PlGF, EGF, TGF-α, AR, BTC, HRGs, HG-EGF, SMDF, OB, CT-1, CNTF, OSM, MK, PTN, or their functional, recombinant, chemical equivalents, homologue, or combinations thereof.

The immune response of a subject may be down-regulated to treat any one or combination of known diseases, disorders, or conditions generally characterized by an abnormally active immune response. For instance, it may be desirable to down-regulate the immune response in a subject having an autoimmune disease.

Examples of autoimmune diseases include, without limitation, alopecia areata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome, autoimmune thrombocytopenic purpura, Behcet's disease, bullous pemphigoid, cardiomyopathy, celiac sprue-dermatitis, chronic fatigue syndrome immune deficiency syndrome, chronic inflammatory demyelinating polyneuropathy, cicatricial pemphigoid, cold agglutinin disease, CREST syndrome, Crohn's disease, Dego's disease, dermatomyositis, dermatomyositis (juvenile), discoid lupus, essential mixed cryoglobulinemia, fibromyalgia/fibromyositis, Grave's disease, Guillain-Barre, Hashimoto's thyroiditis, idiopathic pulmonary fibrosis, idiopathic thrombocytopenia purpura, IgA nephropathy, insulin-dependent diabetes (Type I), juvenile arthritis, lupus, Meniere's disease, mixed connective tissue disease, multiple sclerosis (MS), myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

In another aspect of the present invention, the immune system of a subject having an autoimmune disease (e.g., MS) may be down-regulated using vaccine therapy. In the vaccine therapy, mature DCs are generated from progenitor cells that are toxic to T-cells. The toxic mature DCs are generated by conditioning the progenitor cells in a culture medium. The culture medium can include, for example, SCF and IL-6, Flt3-L and GMSCF, or Flt3-L and GMSCF and IL6. The mature DCs conditioned in the culture medium can be administered to a subject being treated in a vaccine to down-regulate an immune response.

Figure 5:
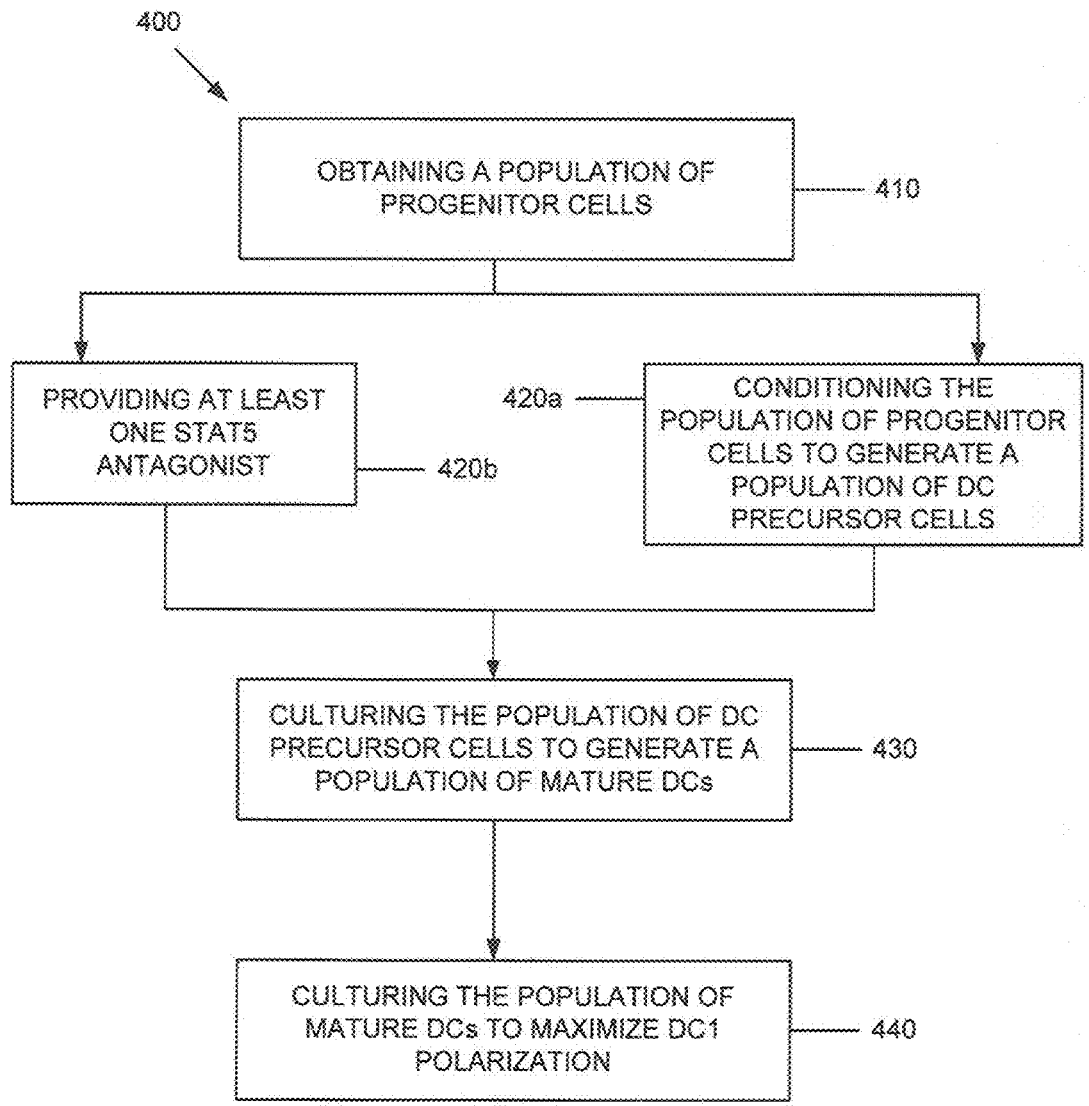
FIG. 5 is a flowchart illustrating a method for generating a population of mature DCs in accordance with the present invention.
Figure 19:
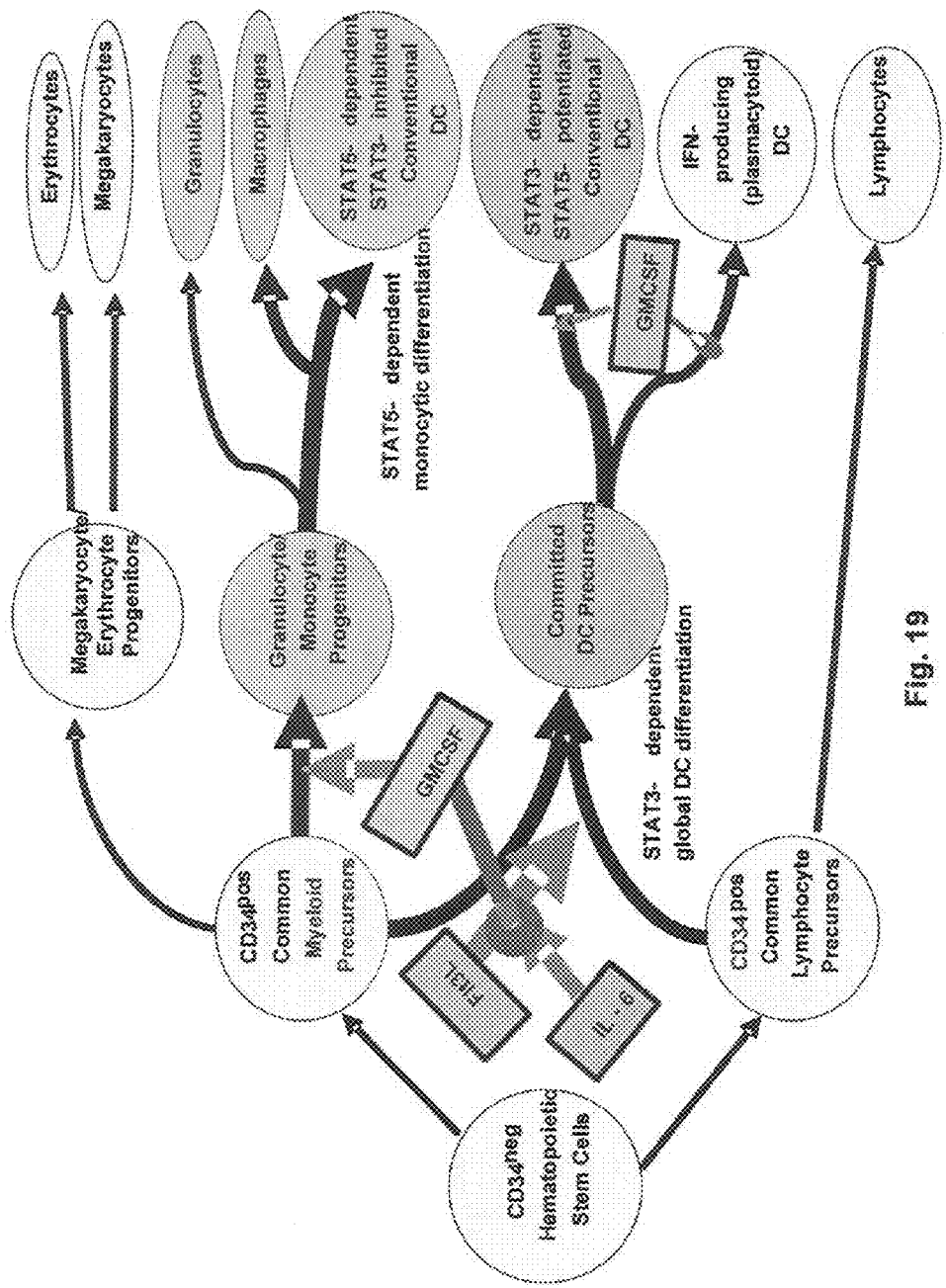
FIG. 19 is a schematic representation of postulated STAT-dependent DC differentiation pathways.
Figure 20:
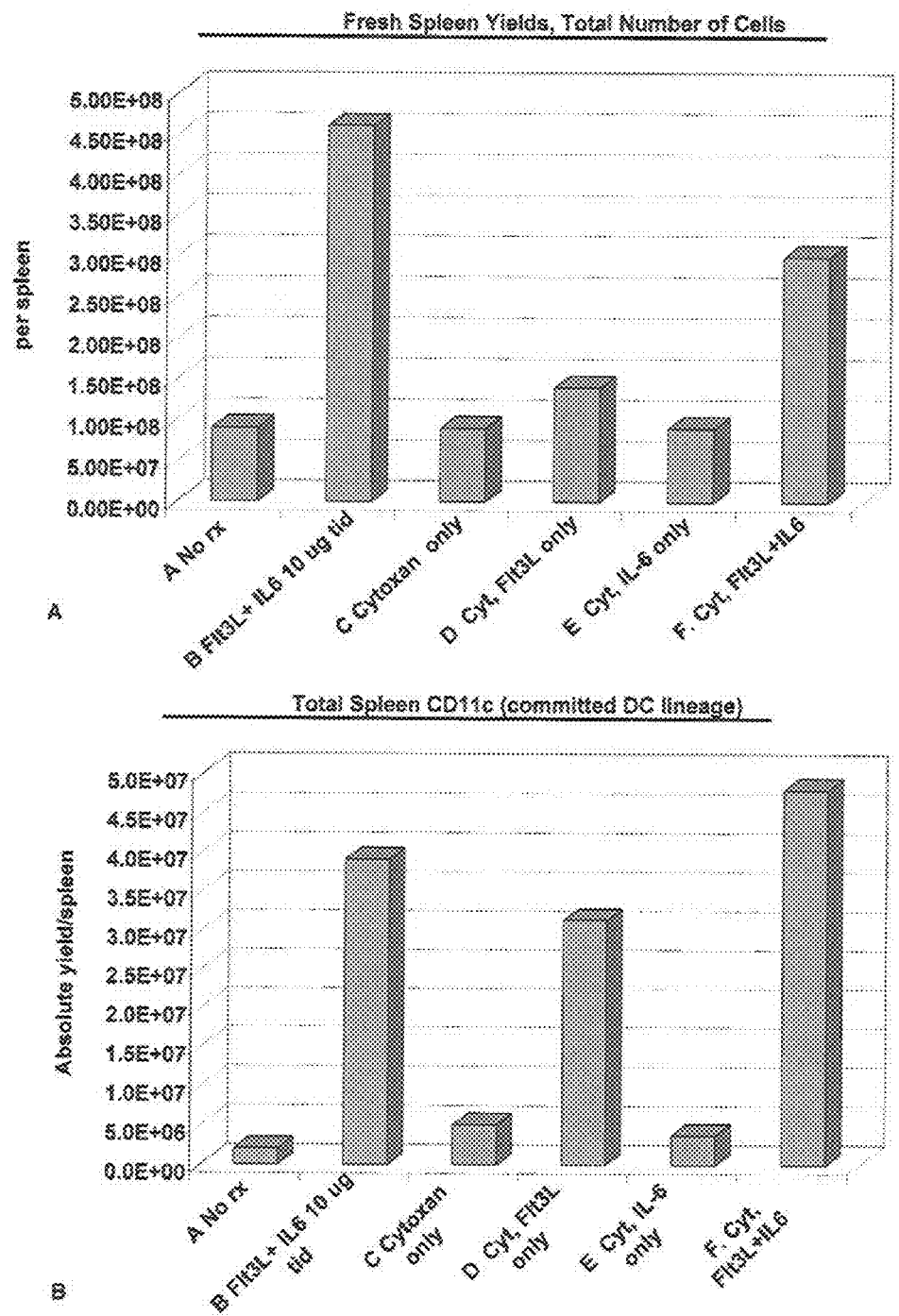
FIGS. 20A-C are bar graphs showing normal BALB/c mice which were treated or untreated with chemotherapy (100 mg/kg cyclophosphamide, a.k.a. cytoxan), then either treated with Flt3-L 10 mcg/i.p. daily, IL-6 alone 10 mcg three times i.p. daily, or combined Flt3-L+IL-6 for six days. Mice were euthanized and spleens counted and analyzed for content of CD11c$^{pos}$ cells (committed DC lineage) and CD34$^{pos}$ cells (stem cells, potential DC precursors) quantified. Although total spleen cell yields were higher following Flt3-L+IL-6 conditioning in the absence of cytoxan, higher percentages and absolute yields of both CD11c$^{pos}$ and CD34$^{pos}$ cells were observed following cytoxan/Flt3-L+IL-6.
Figure 20:
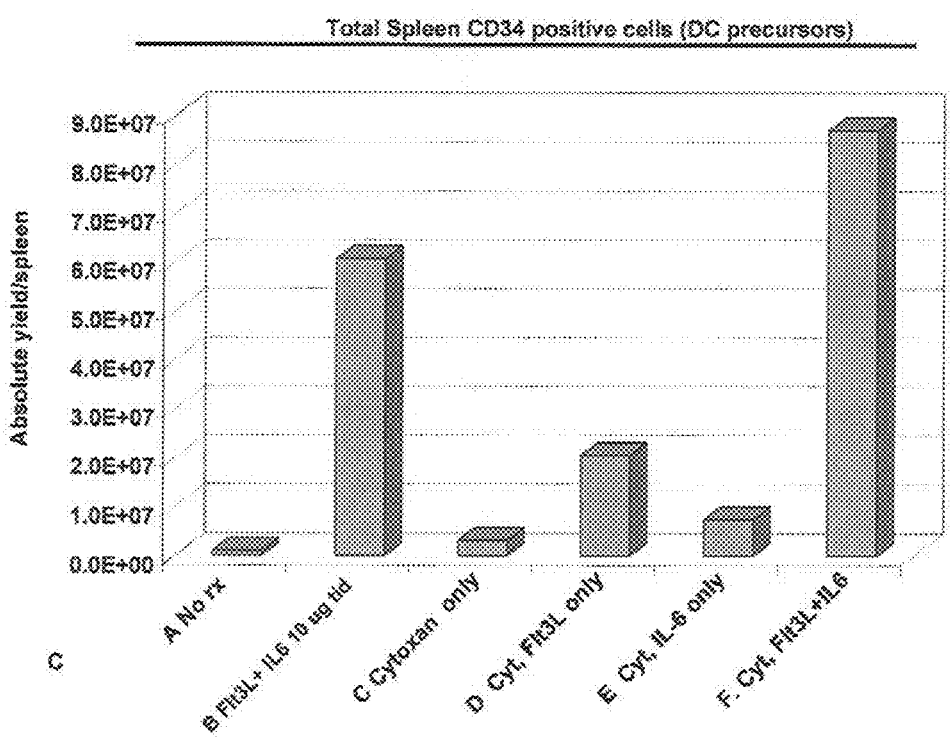
Figure 21:
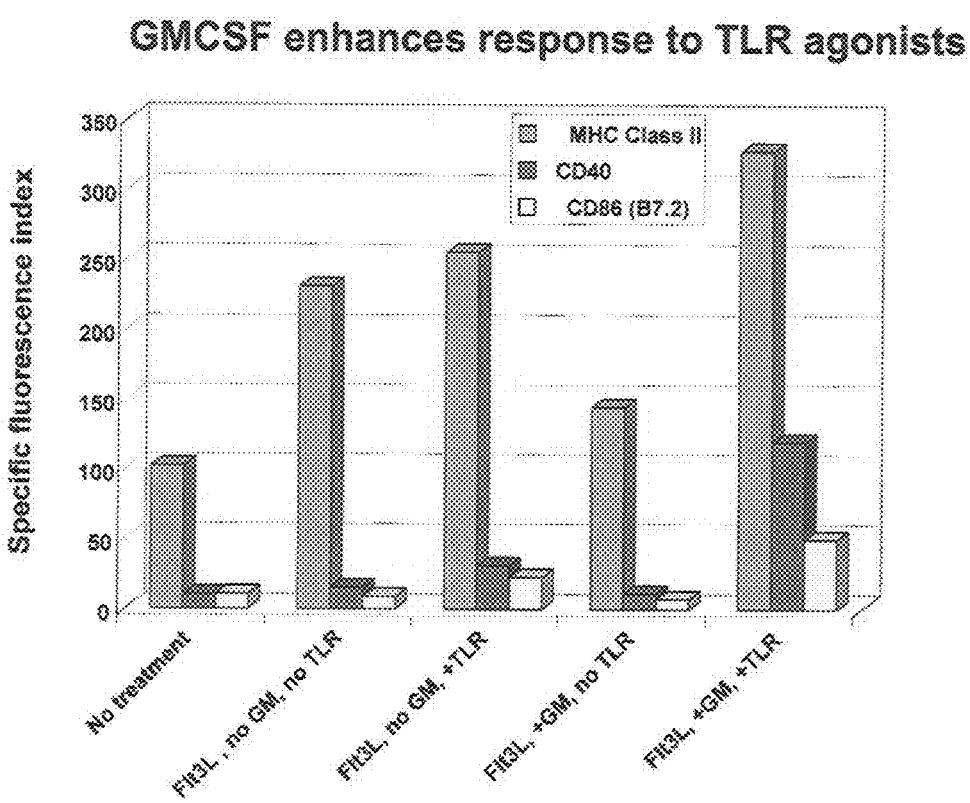
FIG. 21 is a bar graph showing in vivo responses to TLR agonists. Mice were injected for 6 days with 10 mcg i.p. rhFlt3-L or no treatment. On the subsequent day, some mice were treated with a single i.p. injection for rmGMCSF 12 mcg. On the subsequent day, some mice were injected with i.p. with 50 mcg CpG (ODN 1826) and 100 mcg pI:C. Two TLR agonists previously demonstrated to synergize for DC activation. The next day, mice were euthanized and spleens counted and analyzed by FACS for the activation status of the CD11c$^{pos}$ (committed DC) subpopulation. MHC Class II, CD40, and CD86 (B7.2) were co-analyzed. These maturation markers were most activated following TLR agonist treatment, but the latter impact was further enhanced if prior GMCSF treatment had been performed. These impacts were observed in 2 experiments.
Figure 22:
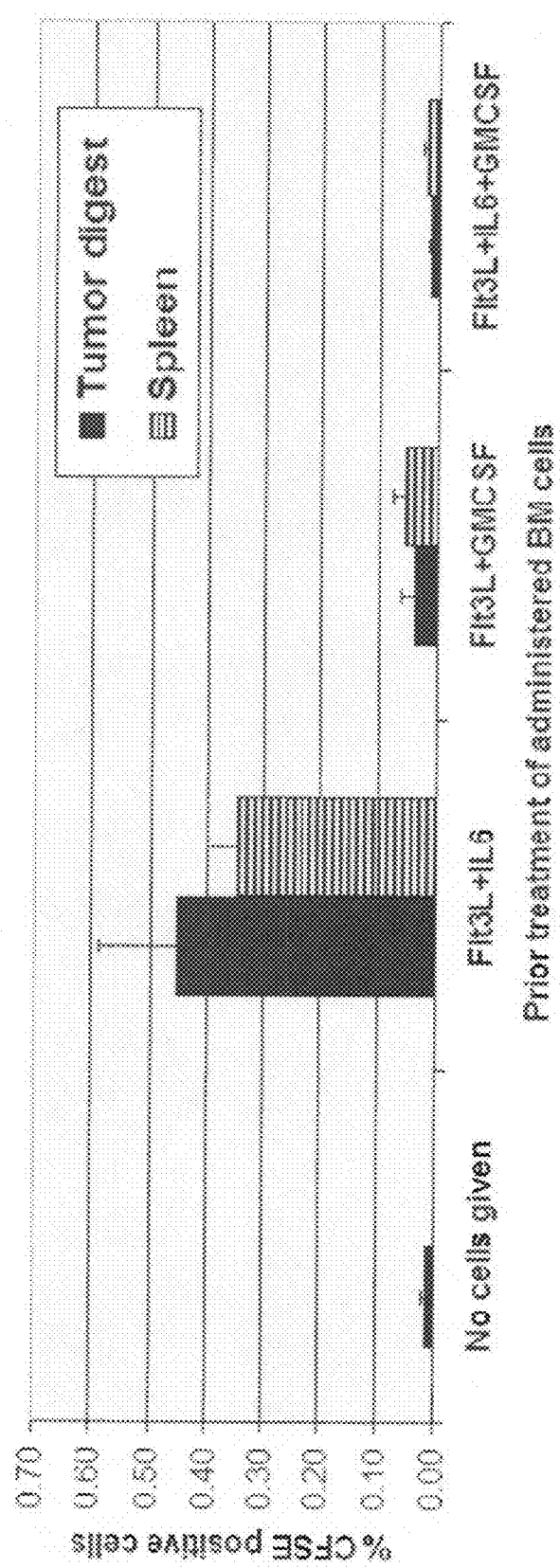

FIG. 5 illustrates a method 400 for generating a mature DC population in accordance with an aspect of the invention. In the method 400, at 410 and 420a, respectively, progenitor cells are obtained and conditioned to generate a population of DC precursors in a manner similar to the method 10. At 420b, at least one signal transducer and activator of transcription 5 (STAT5) antagonist can be contacted with the population of progenitor cells being conditioned at 420a. Contacting the population of progenitor cells with at least one STAT5 antagonist can prevent STAT5 subversion of the STAT3-dependent pathway (FIG. 19).

As used herein, the term "STAT5" can refer to any STAT5, STAT5A or STAT5B protein or polypeptide, or any polynucleotide encoding a STAT5, STAT5A or STAT5B protein or polypeptide.

As used herein, the term "STAT5 antagonist" can refer to any agent or substance which directly or indirectly inhibits or decreases the activity of STAT5 or STAT5 signaling. Examples of STAT5 antagonists can include, but are not limited to: RNA interference reagents (e.g., siRNAs, microRNAs, shRNAs, antisense RNAs) to induce knockdown of a STAT5 polypeptide and/or a polynucleotide encoding a STAT5 polypeptide, examples of which are described in U.S. Pat. No. 7,176,303, the entirety of which is hereby incorporated by reference; ribozyme molecules designed to catalytically cleave STAT5-encoding mRNAs; antibodies or antibody fragments that bind STAT5; and small molecules or drugs that interfere with or inhibit the activity of STAT5.

In an example of the method 400, the STAT5 antagonist can comprise an anti-GMCSF agent. An anti-GMCSF agent can include any agent or substance which directly or indirectly inhibits or decreases the activity of a GMCSF polypeptide or a polynucleotide encoding GMCSF. Examples of anti-GMCSF agents are known in the art and can include, without limitation, GMCSF antibodies or antibody fragments, such as those available from Santa Cruz Biotechnology, Inc. (Santa Cruz, Calif.), as well as RNAi reagents, such as anti-GMCSF shRNAs, available from InvivoGen (San Diego, Calif.), and anti-GMCSF siRNA (available from Santa Cruz Biotechnology, Inc.). At 420b, the anti-GMCSF agent can be contacted with the population of progenitor cells being conditioned at 420a. GMCSF signals through JAK2 and STAT5 to stimulate the expression of STAT5 target genes during monocyte/macrophage differentiation. By contacting the population of progenitor cells being conditioned at 420a with the anti-GMCSF agent, subversion of the STAT3-dependent pathway by STAT5 can be prevented or reduced. Preventing or reducing subversion of the STAT3-dependent pathway by STAT5 can promote DC precursor formation and prevent or reduce mature DC formation.

At 430, a mature DC population can be generated in a manner similar to the method 100. Unlike the step at 130, however, at least one cytokine and/or growth factor can be contacted with the population of DC precursors to terminate STAT3 activation and thereby transition the population of DC precursors into STAT5 activation. For example, GMCSF can be added to the population of DC precursors after 420a and 420b. The addition of GMCSF to the population of DC precursors can terminate STAT3 activation and promote STAT5 activation. By promoting STAT5 activation, the population of DC precursors can differentiate into mature DCs having maximal DC1 function for anti-tumor immunity, for example.

At 440, at least one agent can then be contacted with the mature DC population to further promote DC1 polarization. The at least one agent can include, but is not limited to, a TLR agonist, a cytokine, and a growth factor. Examples of the at least one agent can include TLR8 agonists such as resiquimod, TLR4 agonists such as lipopolysaccharide, TLR3 agonists such as poly I:C, IFN-γ, combinations of TLR8 and TLR4 agonists, combinations of TLR8 and TLR3 agonists, and combinations of TLR8 agonists and IFN-γ.

In another aspect of the present invention, a pharmaceutical composition comprising Flt3-L, IL-6 and a STAT5 antagonist is provided. As used herein, "pharmaceutical composition" refers to a "therapeutically effective amount" of the active agent(s), i.e., Flt3-L, IL-6 and a STAT5 antagonist, together with a pharmaceutically acceptable carrier or diluent. A "therapeutically effective amount" as used herein refers to that amount which provides a therapeutic effect for a given condition or disease and administration regimen. A pharmaceutically acceptable carrier or diluent is one that has met the required standards of toxicological and manufacturing testing, or that it is included on the Inactive Ingredient Guide prepared by the U.S. Food and Drug administration.

In another aspect of the present invention, a method is provided for treating a subject. One step of the method includes administering to the subject a therapeutically effective amount of a pharmaceutical composition comprising Flt3-L, IL-6 and a STAT5 antagonist. As used herein, the term "subject" refers to any warm-blooded organism including, but not limited to, human beings, rats, mice, dogs, goats, sheep, horses, monkeys, apes, rabbits, cattle, etc. The pharmaceutical composition can be administered to the subject using any route and method known in the art including, for example, parenterally, paracancerally, transmucosally, transdermally, intramuscularly, intravenously, intradermally, subcutaneously, intraperitonealy, intraventricularly, intracranially, intravaginally or intratumorally. The pharmaceutical composition comprising Flt3-L, IL-6 and a STAT5 antagonist can be administered to the subject to treat any one or combination of diseases or conditions including, for example, cancer, autoimmune diseases, and pathogenic infections (examples of which are provided above).

In another aspect of the present invention, a chemotherapeutic agent can be administered to a population of progenitor cells prior to conditioning the population of progenitor cells at 30, 120, 220, 320 and 420. Conventional chemotherapy such as cyclophosphamide, for example, can be toxic for both normal proliferating bone marrow components and tumor cells. Chemotherapy can also be toxic for host components, such as regulatory T cells and myeloid suppressor cells, which are also responsible for impairing the immune response. Administering a chemotherapeutic agent to a subject can not only have a cytoreductive effect upon tumor cells, but may also enhance the immune response in the subject by reducing host suppressor elements. Accordingly, one aspect of the present invention can include administering a chemotherapeutic agent, such as cyclophosphamide, to a subject to attack both tumor cells and host suppressor elements. Following administration of cyclophosphamide, Flt3-L and IL-6 can then be administered to condition $CD34^{pos}$ stem cells, for example, during the recovery of the $CD34^{pos}$ stem cells. It will be appreciated that prostaglandin-inhibiting agents, such as glucocorticoids and NSAIDs, for example, may also be contacted with DCs since Flt3-L and IL-6 conditioned DCs may be at least partially susceptible to inhibition by prostaglandins.

It will also be appreciated that certain variations of the present inventive methods may be employed to stimulate DC precursor proliferation. The presence of a tumor can "substitute" for exogenous IL-6 and thereby lead to greater DC precursor proliferation as a variety of tumors can activate STAT3 in DCs. Thus, Flt3-L alone may be administered to a population of progenitor cells, such as $CD34^{pos}$ stem cells, to promote DC precursor proliferation. Additionally, it should be appreciated that DC proliferation may be improved or increased by substituting longer acting IL-6 analogs, such as hyperIL-6, for IL-6. Such analogs may have more favorable kinetics (as compared to IL-6) and, therefore, promote enhanced DC precursor proliferation.

The following examples are for the purpose of illustration only and are not intended to limit the scope of the claims, which are appended hereto.

EXAMPLE 1

Dendritic cells (DCs) are the most potent antigen (Ag)-presenting cells in the body and have been employed in many tumor vaccine immunotherapy trials, sometimes with therapeutic impacts (Rosenberg, S A et al. *Nat. Med.* 10, 909-915 (2004)). However, DCs prepared from various sources display a wide range of characteristics in vitro and in vivo, and it remains uncertain which characteristics are most likely to promote successful immunotherapy (Xu, S. et al. *J. Immunol.* 171, 2251-2261 (2003); Bonifaz, L. et al. *J. Exp. Med.* 196, 1627-1638 (2002)).

In vitro, a variety of single agents, including CD40 ligand, Toll-like receptor (TLR) agonists, or calcium ionophore, can induce DC phenotypic maturation (Xu, S. et al. *J. Immunol.* 171, 2251-2261 (2003); Bonifaz, L. et al. *J. Exp. Med.* 196, 1627-1638 (2002); Napolitani, G. et al. *Nat. Immunol.* 6, 769-776 (2005); Czerniecki, B J et al. *J. Immunol.* 159, 3823-3837 (1997); Mailliard, R B et al. *Cancer Res.* 64, 5934-5937 (2004)). Such maturation is manifested by pronounced expression of MHC and costimulatory molecules, CD40 and CCR7 expression, and IL8 secretion, but falls short of the DC's potential to achieve DC1 polarization, the maximally effective state for promoting cell-mediated immunity (Xu, S. et al. *J. Immunol.* 171, 2251-2261 (2003); Napolitani, G. et al. *Nat. Immunol.* 6, 769-776 (2005); Mailliard, R B et al. *Cancer Res.* 64, 5934-5937 (2004)). Besides phenotypic maturation, DC1 polarization results in abundant production of IL12p70 heterodimer and IL23, secretion of the chemokine MIP-1β, and preferential expression of Delta-4 Notch Ligand (Xu, S. et al. *J. Immunol.* 171, 2251-2261 (2003); Napolitani, G. et al. *Nat. Immunol.* 6, 769-776 (2005)). Such DC1 products are highly associated with the chemokine attraction and activation of T1-type $CD4^{pos}$ and $CD8^{pos}$ T cells; in particular, production of IL-12p70 heterodimer is critical for the sensitization of high avidity T cells which can directly recognize and kill tumor targets (Xu, S. et al. *J. Immunol.* 171, 2251-2261 (2003); Napolitani, G. et al. *Nat. Immunol.* 6, 769-776 (2005); Gajewski, T F et al. *J. Immunol.* 154, 5637-5648 (1995)).

Although desirable for anti-tumor immunity, DC1 polarization is more readily signaled by infectious agents than by tumor. Immature DCs use their capacity to recognize pathogen-associated molecular patterns (PAMPs) through TLRs to assess the likelihood of host infection and the appropriateness of DC1 polarization (Napolitani, G. et al. *Nat. Immunol.* 6, 769-776 (2005)). Individual TLRs signal DCs primarily through the MyD88 pathway (e.g., TLR7, TLR8 and TLR9) or the TRIF pathway (e.g., TLR3) with TLR4 evidencing elements of pathway duplicity (Napolitani, G. et al. *Nat. Immunol.* 6, 769-776 (2005)). While activation of either pathway is often sufficient to induce phenotypic DC maturation, only dual activation of MyD88 and TRIF pathways, or single pathway activation potentiated by exposure to IFNγ or CD40 ligation, assures robust DC1 polarization (Napolitani, G. et al. *Nat. Immunol.* 6, 769-776 (2005)).

Fresh mobilization of DC1 precursors is an attractive strategy to promote cross-presentation of tumor Ags both within the tumor bed and in tumor-draining lymph nodes (TDLN). Recent studies have evidenced the capacity of stem cell mobilizing treatments, notably granulocyte-macrophage colony stimulating factor (GMCSF), granulocyte colony stimulating factor (GCSF), Flt3 ligand (Flt3L), and Flt3L+GMCSF to augment the numbers of circulating DC precursors (Lonial, S. et al. *Biol. Blood Marrow Transplant* 10, 848-857 (2004); Avigan, D. et al. *Clin. Cancer Res.* 5, 2735-2741 (1999); Pulendran, B. et al. *J. Immunol.* 165, 566-572 (2000); Gasparetto, C. et al. *Cytokine* 18, 8-19 (2002); Parajuli, P. et al. *Exp. Hematol.* 29, 1185-1193 (2001); Robinson, S. et al. *J. Hematother. Stem Cell Res.* 9, 711-720 (2000); Berhanu, A. et al. *Cancer Res.* 66, 4895-4903 (2006)), but the potential of such mobilized precursors to achieve DC1 polarization is presently unclear. For example, Flt3L+GMCSF mobilization was recently observed to induce abundant infiltration of DCs into mouse tumors, but such DCs retained an immature phenotype, activated regulatory T cells, and promoted tumor growth (Berhanu, A. et al. *Cancer Res.* 66, 4895-4903 (2006)). Because immunosuppressive factors such as IL10, TGF-β, VEGF and $PGE_2$ are often produced within the tumor milieu, such factors may prevent mobilized precursors from attaining maturation and DC1 polarization (Kao, J Y et al. *J. Immunol.* 170, 3806-3811 (2003); Kobie, J J et al. *Cancer Res.* 63, 1860-1864 (2003); Gabrilovich, D. et al. *Blood* 92, 4150-4166 (1998); Dikov, M M et al. *J. Immunol.* 174, 215-222 (2005); Shurin, M R et al. *Int. J. Cancer* 101, 61-68 (2002); Yang, A S et al. *Cancer Res.* 63, 2150-2157 (2003); Kalinski, P. et al. *J. Immunol.* 161, 2804-2809 (1998)). However, other evidence suggests that proliferative treatments themselves may influence the later differentiation responses of mobilized stem cells (Lonial, S. et al. Biol. *Blood Marrow Transplant* 10, 848-857 (2004); Avigan, D. et al. *Clin. Cancer Res.* 5, 2735-2741 (1999); Pulendran, B. et al. *J. Immunol.* 165, 566-572 (2000); Gasparetto, C. et al. *Cytokine* 18, 8-19 (2002); Parajuli, P. et al. *Exp. Hematol.* 29, 1185-1193 (2001); Robinson, S. et al. *J. Hematother. Stem Cell Res.* 9, 711-720 (2000); Berhanu, A. et al. *Cancer Res.* 66, 4895-4903 (2006)). We therefore postulated that certain proliferative treatments might license rather than limit responsiveness to classic as well as to non classic DC1 polarization stimuli.

Stem cell proliferation is inducible through several signaling pathways, including receptor-linked tyrosine kinases (e.g., Flt3-ligand, SCF) (Ebihara, Y. et al. *Blood* 90, 4363-4368 (1997); Sui, X et al. *Proc. Natl. Acad. Sci.* 92, 2859-2863 (1995); Brasel, K. et al. *Blood* 90, 3781-3788 (1997); Hudak, S. et al. *Blood* 85, 2747-2755 (1995)), the tall cytokine receptor gp130 (e.g., IL6) (Ebihara, Y. et al. *Blood* 90, 4363-4368 (1997); Sui, X et al. *Proc. Natl. Acad. Sci.* 92, 2859-2863 (1995); Skiniotis, G. et al. *Nat. Struct. Mol. Biol.* 12, 545-551 (2005)), and the hematopoetin receptor superfamily (e.g., GMCSF) (Brasel, K. et al. *Blood* 90, 3781-3788 (1997); Martinez-Moczygemba, M. et al. *J. Allergy Clin. Immunol.* 112, 653-665 (2003); Guthridge, M A et al. *Blood* 103, 820-827 (2004)). During the systematic testing of such signaling agents we identified that combined exposure to Flt3L plus interleukin-6 (Flt3L+IL6) not only synergized for stem cell proliferation, but also broadly licensed CD34$^{pos}$ stem cells to achieve post-proliferative DC1 polarization. Paradoxically, co-conditioning with GMCSF, instead of or in addition to IL6, abrogated the post-proliferative DC1 licensing impacts of Flt3L+IL6 conditioning.

EXAMPLE 2

Synergistic Induction of CD34$^{pos}$ Stem Cell Proliferation

Figure 6:
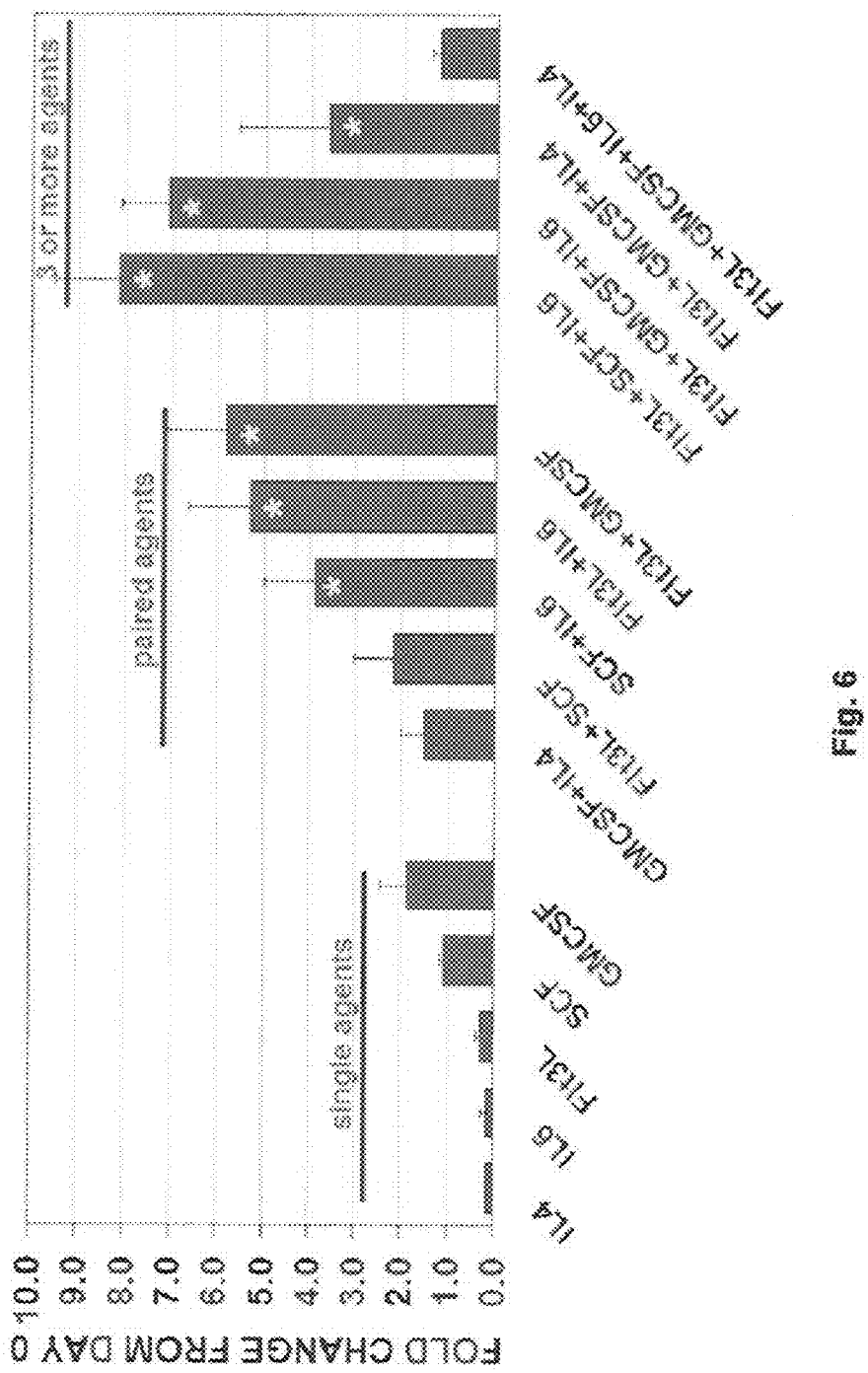
FIG. 6 is a chart showing numeric expansion resulting from the exposure of bone marrow (BM) suspensions to various factors. BM freshly harvested from C57BL/6 mice was cultured for 6 days in the specific factors, then harvested and counted. Each bar represents 3-11 determinations±s.d., each performed in synchronous comparison to at least five other groups. Asterixed bars indicate treatment combinations which displayed proliferative synergy. Synergistic expansions reflected a 35-80 fold selective outgrowth of the $CD34^{pos}$ subpopulation (see FIG. 10)
Figure 10:
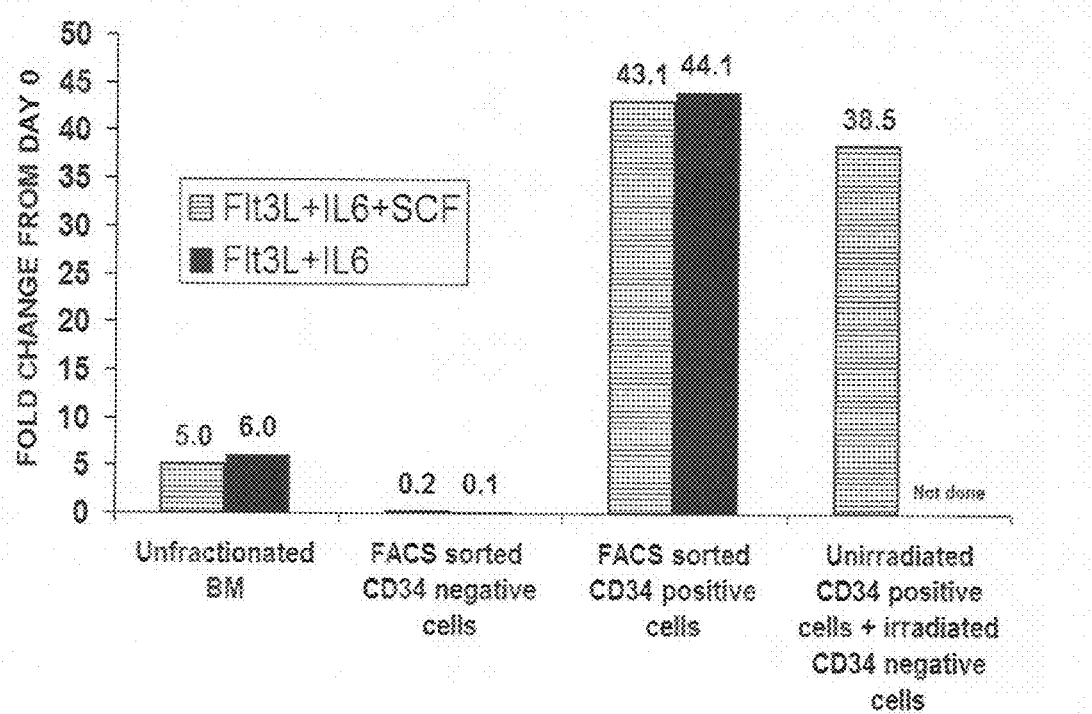
FIG. 10 is a histogram showing gross numeric expansion of fresh bone marrow (BM) reflective of selective outgrowth of the $CD34^{pos}$ subpopulation. Freshly prepared mouse BM cell suspensions were stained with FITC-anti-CD34 mAb to enable isolation of $CD34^{pos}$ and $CD34^{neg}$ subpopulations by a FACSAria cell sorter. $CD34^{pos}$ cells initially represented 10.8±7% of the total BM cells. The following groups were then cultured for 6 days in 75 cm² flasks, either in Flt3L+SCF+IL6 (striped bars) or in Flt3L+IL6 (solid bars): "Unfractionated BM" (12-15 million per flask); "FACS sorted $CD34^{neg}$ cells" (12-15 million per flask); "FACS sorted $CD34^{pos}$ cells" (2-3 million per flask); or "FACS sorted, unirradiated $CD34^{pos}$ cells plus irradiated (3,000 cGy) $CD34^{neg}$ cells." Labels above bars indicate fold numeric expansion during the 6 day culture. The composite data indicate that all numeric expansion observed under these conditions was attributable to proliferation of the $CD34^{pos}$ subpopulation, with no requirement for a $CD34^{neg}$ feeder layer. (Not done=group not done)

We cultured fresh mouse BM in two stages, a 6-7 day proliferative phase (Step 1) and a 2-3 day post-proliferative phase (Step 2). Consistent with previous reports (Ebihara, Y. et al. *Blood* 90, 4363-4368 (1997); Sui, X et al. *Proc. Natl. Acad. Sci.* 92, 2859-2863 (1995); Brasel, K. et al. *Blood* 90, 3781-3788 (1997); Hudak, S. et al. *Blood* 85, 2747-2755 (1995)), several treatment pairings (Flt3L+IL6, SCF+IL6, or Flt3L+GMCSF) synergistically induced numeric expansion during Step 1 culture (FIG. 6). FACS sorting experiments confirmed that such expansion represented a net 35-80 fold proliferation of the minor (<12%) CD34$^{pos}$ stem cell subpopulation, with rapid dropout of the initially CD34$^{neg}$ subpopulation (FIG. 10). Stem cell proliferation persisted well past day 7 if medium and factors were adequately replenished (not shown).

Even though Flt3L is highly myeloproliferative when administered as a single agent to animals (Berhanu, A. et al. *Cancer Res.* 66, 4895-4903 (2006); Maraskovsky, E. et al. *J. Exp. Med.* 184, 1953-1962 (1996)), Step 1 culture with single agent Flt3L yielded only a fraction of culture input, even when Flt3L dosing was extended up to 300 ng/ml (FIG. 6 and not shown). This was consistent with previous reports that single agent Flt3L is poorly proliferogenic in vitro unless a higher starting BM density confers an occult source of IL6 (Hudak, S. et al. *Blood* 85, 2747-2755 (1995); Brasel, K. et al. *Blood* 96, 3029-3039 (2000)).

Figure 11:
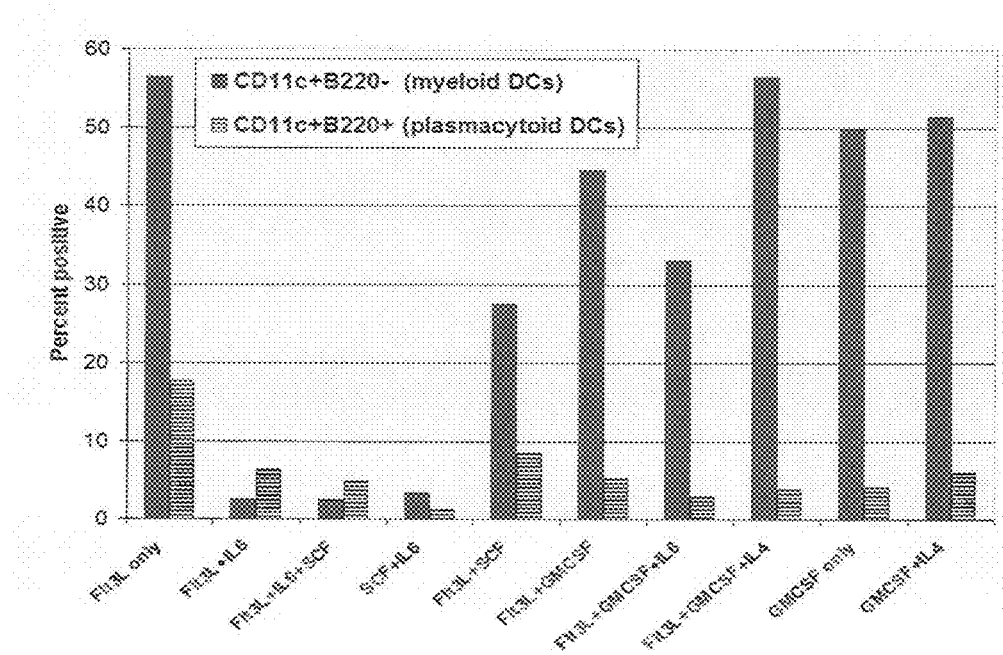
FIG. 11 shows contrasting surface expression profiles of BM cells following 6 day exposure to various Step 1 conditioning treatments. Specifically.

Prior to initial culture, freshly harvested CD34$^{pos}$ BM cells displayed only rare cells with differentiation markers such as CD11c and MHC Class II (not shown). It was observed that this undifferentiated state was best maintained during Step 1 proliferation when IL-6 was present and GMCSF was absent as a conditioning factor (FIG. 11). When, in contrast, elements of DC differentiation became prominent during Step 1 culture, they included both myeloid (CD11c$^{pos}$/B220$^{neg}$) and plasmacytoid (CD11c$^{pos}$/B220$^{pos}$) elements (FIG. 11).

DC1 Polarization Potential Varies as a Consequence of BM Conditioning

Following Step 1 conditioning, BM cultures were washed thoroughly and exposed to TLR agonists to test the cells' potential for DC maturation and IL-12 production during Step 2 culture. Since TLR9 and TLR4 were invariably expressed by mouse BM cells at the end of Step 1 cultures (not shown), we standardly employed CpG (ODN 1826) and lipopolysaccharide (LPS) to stimulate coordinate activation of MyD88 and TRIF pathways (Napolitani, G. et al. *Nat. Immunol.* 6, 769-776 (2005)).

Whether proliferative or nonproliferative, Step 1 treatments defined the subsequent Step 2 response to TLR agonists. After any Step 1 treatment, at least a fraction of cells proved capable of pronounced MHC, co-stimulatory molecule and CD40 upregulation when TLR stimulated. However, most Step 1 conditions led to large proportions of cells remaining unresponsive or hyporesponsive to TLR agonists, either null for MHC Class II expression or arrested at an immature DC phenotype (FIG. 6/FIG. 11). Gr1 expression was a common feature of poorly responsive subpopulations (FIG. 11) (Kusmartsev, S. et al. *J. Immunol.* 172, 989-999 (2004); Serafini, P. et al. *Cancer Res.* 64, 6337-6343 (2004)).

A pronounced dichotomy was evident for GMCSF vs. Flt3L conditioning, with GMCSF producing infrequent and/or blunted responses to the TLR agonists, in contrast to Flt3L's nearly global licensing for pronounced TLR reactivity. Despite the proliferative synergy evident when GMCSF and Flt3L were given together as conditioning agents (FIG. 6), GMCSF effectively abrogated such Flt3L licensing, resulting in numeric expansion of cells with a much more limited potential for DC maturation. GMCSF antagonism to Flt3L was strictly limited to the conditioning/proliferative phase of culture, since its routine addition later during Step 2 culture was not at all inhibitory.

Figure 12:
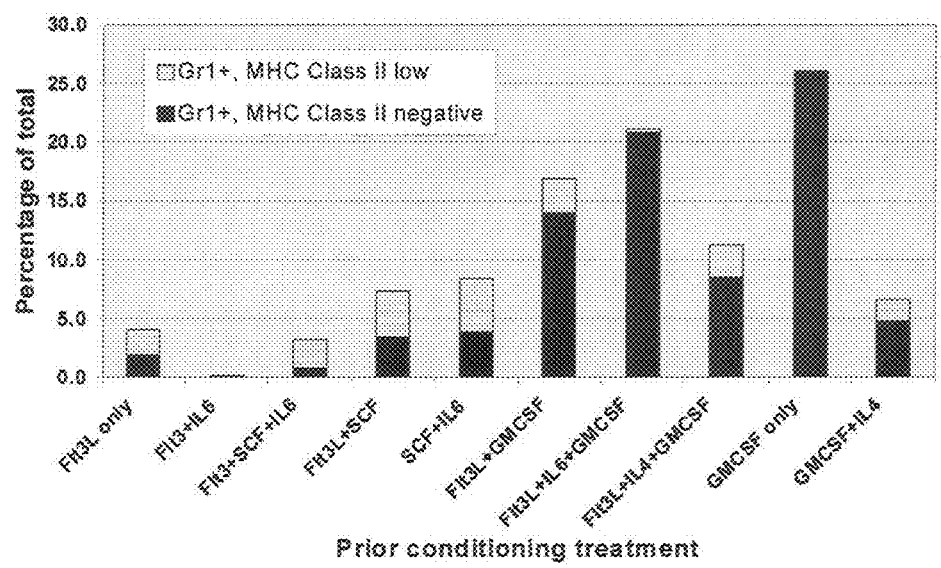
FIG. 12 shows maturation profiles of BM cells following Step 2 culture in DC1 polarizing stimuli. Specifically.

In contrast to GMCSF, IL6 not only synergized with Flt3L to stimulate marked stem cell proliferation, but was also fully permissive for DC1 licensing. Following Flt3L+IL6 conditioning, virtually all proliferated stem cells achieved pronounced DC phenotypic maturation upon CpG+LPS stimulation (FIG. 12, compare to earlier timepoint (FIG. 11), and the vast majority also participated in IL-12 production. IFNβ was co-elicited rather than IFNα production by all tested TLR agonist combinations, indicating that myeloid DC differentiation was the dominant response to these stimuli. Flt3L+IL6's licensing impact, but not its proliferative impact, was also abrogated by co-conditioning with GMCSF (FIG. 12).

Conditioning in Flt3L or Flt3L+IL6 Decreases Requirements for Exogenous Maturation Factors DC differentiation typically arrests at the immature stage unless DCs are exposed to additional signals such as CD40 ligation, calcium ionophore or TLR agonists (Xu, S. et al. *J. Immunol.* 171, 2251-2261 (2003); Bonifaz, L. et al. *J. Exp. Med.* 196, 1627-1638 (2002); Napolitani, G. et al. *Nat. Immunol.* 6, 769-776 (2005); Czerniecki, B J et al. *J. Immunol.* 159, 3823-3837 (1997); Mailliard, R B et al. *Cancer Res.* 64, 5934-5937 (2004)). It was observed, however, that BM cells conditioned in single agent Flt3L displayed a spontaneous tendency to complete DC maturation during Step 2 culture, even in the absence of such exogenous maturation stimuli. Remarkably, proliferative conditioning in Flt3L+IL6 licensed similar spontaneous maturation during Step 2 culture, even though co-exposure to IL6 had potently suppressed MHC Class II and CD11c expression during Step 1 culture. Instead, uniform upregulation of MHC Class II and CD11c ensued within hours of transfer from Flt3L+IL6 into GMCSF, followed by upregulation of CD40, co-stimulatory molecules and CCR7 between 48 and 72 hours of Step 2 culture. Spontaneous DC maturation conditioned by Flt3L or Flt3+IL6 was even more robust when exogenous IL4 was included during Step 2 culture.

For all other tested proliferative conditioning treatments, spontaneous Step 2 maturation was either attenuated or fully absent. Furthermore, even when conditioning treatments produced elements of DC differentiation during Step 1 culture, as in the case of Flt3L+GMCSF, such elements spontaneously regressed during Step 2 culture unless exogenous maturational stimuli were also provided.

Inclusion of GMCSF as a Step 1 conditioning agent fully abrogated Flt3L or Flt3L+IL6's capacity to license spontaneous DC maturation.

Figure 7:
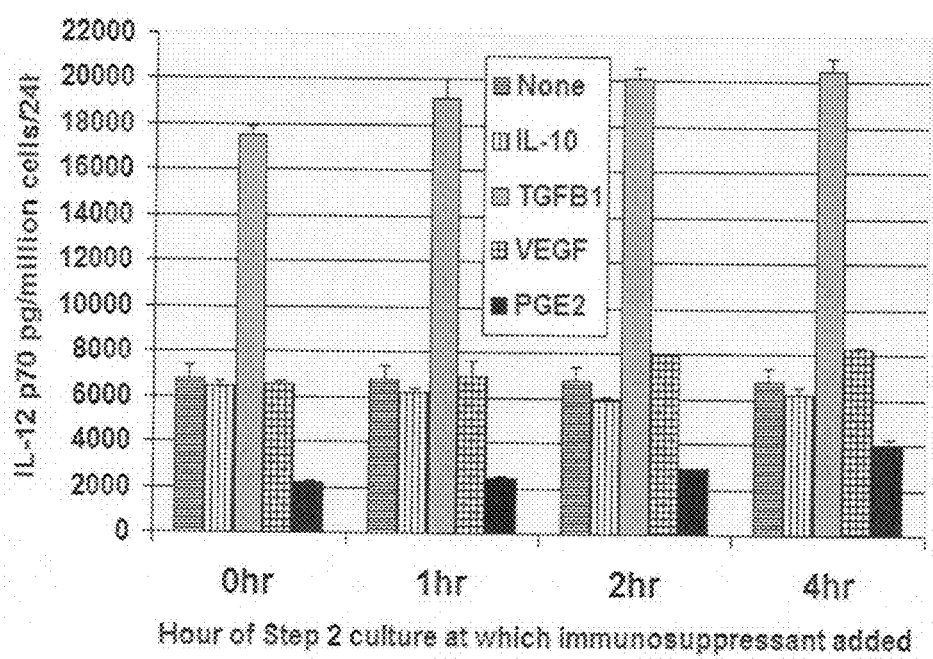
FIG. 7A is a histogram showing Step 2 cultures (cells were re-plated in GMCSF and IL-4 at 0 hr, CpG+LPS added at 24 hr, FACS performed at 44 hr), except that listed immunosuppressive factors were added at 0 hr, 1 hr, 2 hr, or 4 hr of Step 2 culture, and supernatants analyzed by ELISA in triplicate for IL-12 p70 content at 44 hr of Step 2 culture. Error bars indicate s.d. This is representative of three experiments.

Flt3L+IL6 Conditioned DC Precursors Resist Tumor-Associated Immunosuppressive Factors We investigated whether Flt3L+IL6 proliferative conditioning conferred uniform responsiveness to DC1 polarization stimuli even in the presence of putative immunosuppressive factors. We added IL10, TGFβ1 VEGF, or $PGE_2$ at doses which equaled and exceeded those reported to inhibit the maturation of other DC preparations (Kao, J Y et al. *J. Immunol.* 170, 3806-3811 (2003); Kobie, J J et al. *Cancer Res.* 63, 1860-1864 (2003); Gabrilovich, D. et al. *Blood* 92, 4150-4166 (1998); Dikov, M M et al. *J. Immunol.* 174, 215-222 (2005); Shurin, M R et al. *Int. J. Cancer* 101, 61-68 (2002); Yang, A S et al. *Cancer Res.* 63, 2150-2157 (2003); Kalinski, P. et al. *J. Immunol.* 161, 2804-2809 (1998)). IL10 and VEGF exposure had negligible impacts upon DC1 polarization at the doses given, whereas exposure to TGFl31 paradoxically enhanced both phenotypic maturation and IL12 secretion. Only $PGE_2$ exposure substantially inhibited TLR agonist-induced phenotypic DC maturation and IL12 production. Nonetheless, a large subpopulation of Flt3L+IL6 conditioned BM cells could already resist $PGE_2$ inhibition at the beginning of Step 2 culture, and such resistance became progressively more frequent within several hours of Step 2 culture (FIG. 7

Flt3L+IL6 Conditioned DC Precursors Respond to Tumor Contact with Accelerated DC Maturation and DC1 Polarization Because DC ingestion of cellular material can induce tolerogenic DCs (Bonifaz, L. et al. *J. Exp. Med.* 196, 1627-1638 (2002)), we tested the impact of exposing DCs to large volumes of tumor at 16-24 hours of Step 2 culture in GMCSF, to determine tumor's impact on subsequent spontaneous maturation. To cluster plate wells each containing 4 million conditioned BM cells, we added either 4 million freeze-thawed (killed) tumor cells; 3 million irradiated (10,000 cGy), trypan-excluding tumor cells; or 2 million unirradiated, actively proliferating tumor cells. Given the much larger dimensions of viable tumor cells compared to the cultured BM cells, these represented voluminous tumor challenges.

Remarkably, after Flt3L+IL6 conditioning, post-proliferative contact with any of these tumor materials could actually accelerate DC maturation, emulating treatment with a TLR agonist (Napolitani, G. et al. *Nat. Immunol.* 6, 769-776 (2005)). Furthermore, combining tumor exposure with IFNγ treatment could induce IL12 (p70) production, emulating combined treatment with IFNγ plus a TLR agonist (Xu, S. et al. *J. Immunol.* 171, 2251-2261 (2003); Napolitani, G. et al. *Nat. Immunol.* 6, 769-776 (2005)). Neither tumor nor IFNγ treatment alone induced IL12 production (not shown). When other Step 1 conditioning conditions were compared, these activating effects of tumor were either attenuated or completely absent Inclusion of GMCSF as a Step 1 conditioning agent fully abrogated Flt3L+IL6's licensing of this phenomenon.

The unique maturational effect of tumor for Flt3L+IL6 conditioned DC precursors was not attributable to occult endotoxin (not shown). A range of tumor lines stimulated DC maturation after Flt3L+IL6 conditioning, including MCA-205 and MCA-203 sarcomas and B16 melanoma derived from C57BL/6 mice, CT26 colon adenocarcinoma derived from BALB/c mice, and 888me1 from a melanoma patient. Both fresh whole cell tumor digests and established tumor lines were effective for stimulation, indicating that host stromal cells were unessential, and DC maturation could be stimulated whether the tumor challenge was syngeneic, allogeneic or xenogeneic. While fully killed lysate could be employed effectively, viable tumor proved even more effective. Separation of tumor from Flt3L+IL6 conditioned DC precursors by TRANSWELL membranes abrogated the activating effect of tumor, underscoring a requirement for direct contact; in contrast, however, phagocytosis of latex beads did not accelerate maturation (not shown).

Impact of Flt3L+IL6 Conditioned DCs Upon Tumor-Sensitized T Cells

We examined the capacity of variously preconditioned DCs to reverse tolerance in T cells harvested from mice bearing advanced tumors. L-selectin$^{low}$ T cells harvested from tumor-draining lymph nodes (TDLN) are naturally sensitized to the relevant tumor but are also demonstrably tolerized, due to the massive upstream tumor burden (Liu, J. et al. *Cancer Immunol. Immunother.* 46, 268-276 (1998)). In vitro exposure to anti-CD3 coated cluster plates, followed by IL2 stimulation, is a conventional means to reverse tolerance and numerically expand anti-tumor effector T cells (Peng, L. et al. *J. Immunol.* 165, 5738-5749 (2000)). However, such polyclonal anti-CD3 stimulation typically causes CD8$^+$ T cells to overgrow CD4$^+$ T cells, and furthermore lacks the element of Ag presentation to steer outgrowth of tumor-specific T cells (Peng, L. et al. *J. Immunol.* 165, 5738-5749 (2000); Wang, L. et al. *J. Translational Med.* 2, 41 (2004)).

Figure 13:
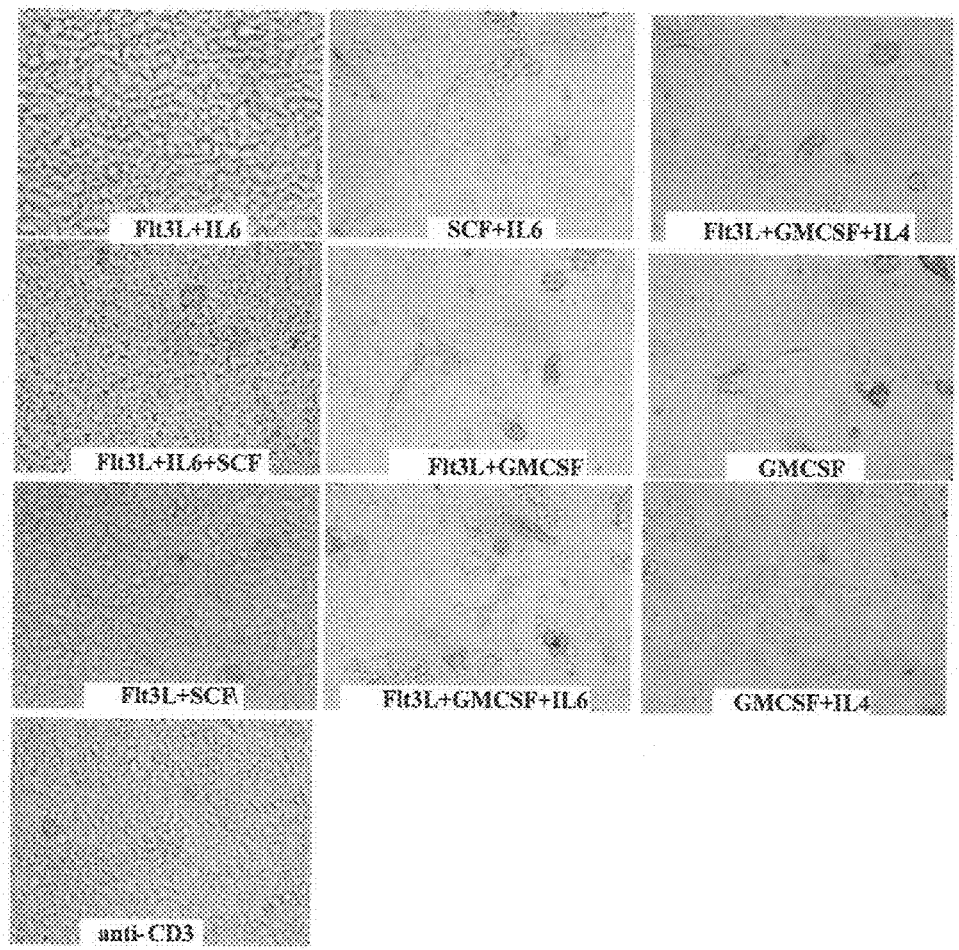
FIGS. 13A-B show T cell expansion.
Figure 13:
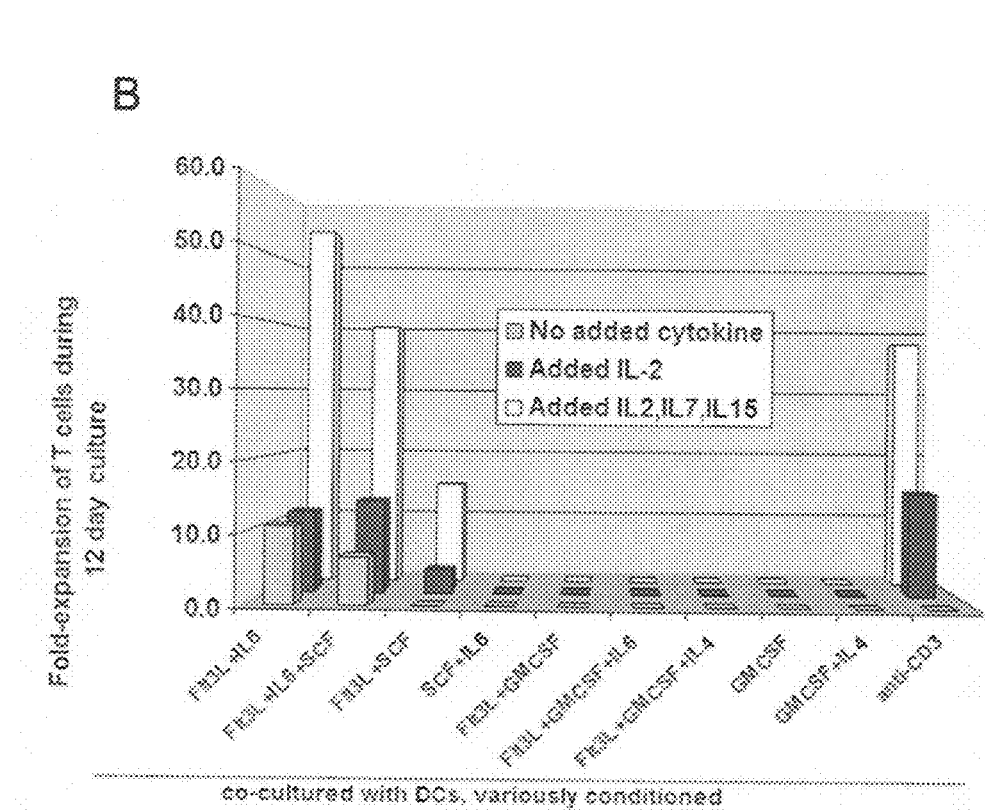
Figure 14:
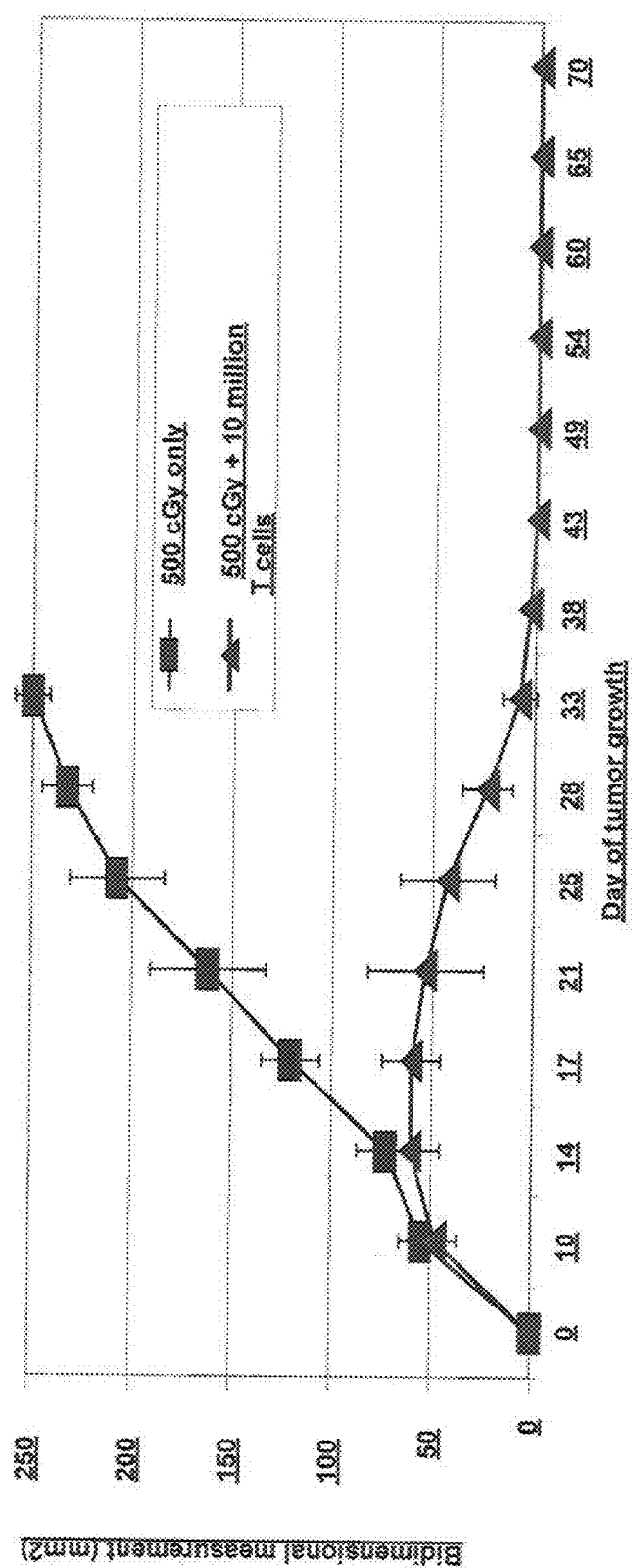
FIG. 14 shows T cell expansion from tumor-bearing mice. Specifially.
Figure 15:
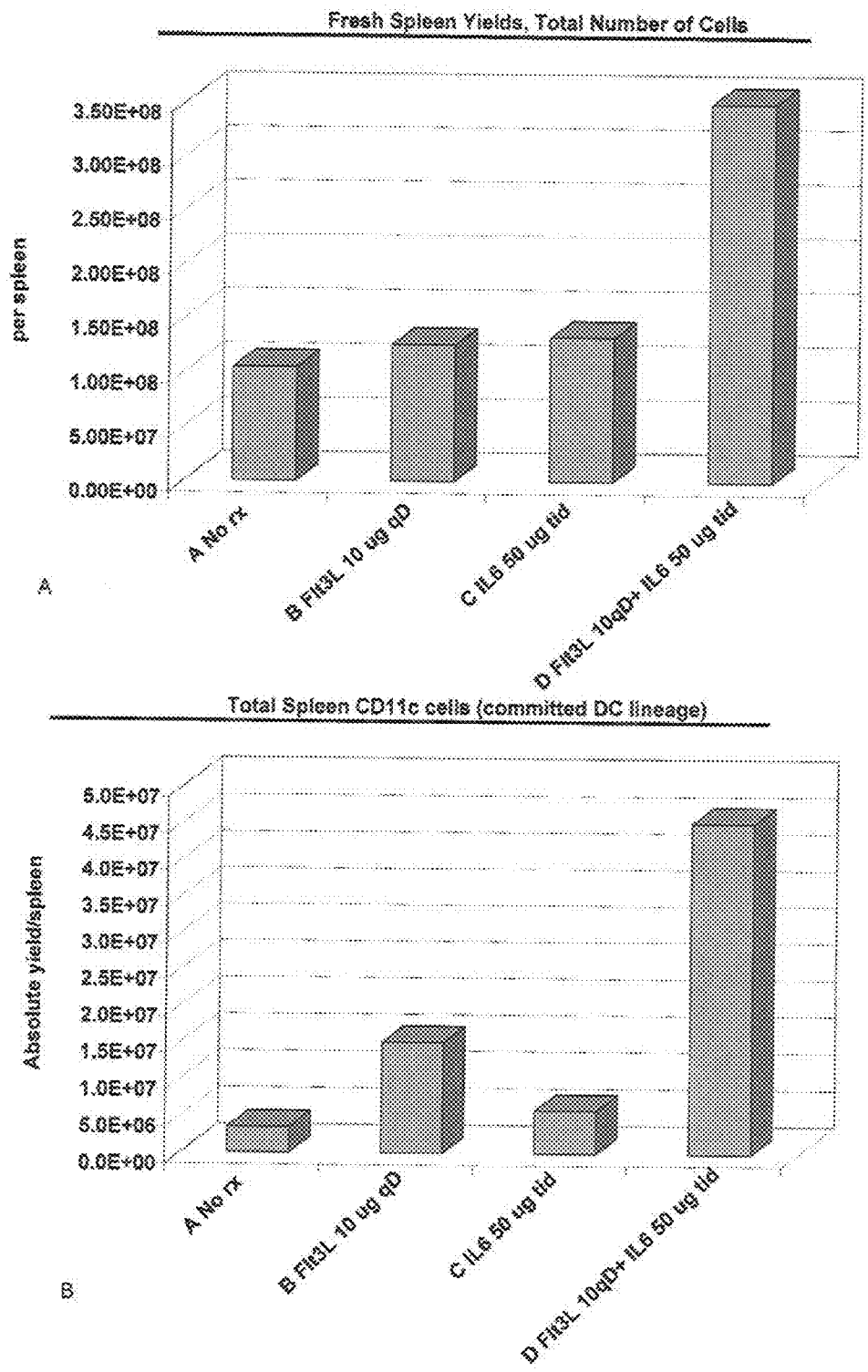
FIGS. 15A-D are a series of graphs showing BALB/c mice treated for six days with either (A) nothing, (B) rhFlt3-L 10 mcg i.p. daily, (C) rhIL-6 mcg i.p. three times daily, and (D) rhFlt3-L 10 mcg i.p. daily plus rhIL-6 50 mcg i.p. three times daily. The next day mice were euthanized, spleens and BM harvested, and CD11c$^{pos}$ cells (committed DC lineage) and CD34$^{pos}$ cells (stem cells, potential DC precursors) quantified. Results are representative of four experiments. The data display the synergy of Flt3-L+IL-6 for generating CD11c$^{pos}$ DCs in vivo, as well as dramatic surge in CD34$^{pos}$ cells which may serve as DC precursors. This is evident in absolute yields in the spleen, whereas within the BM, Flt3-L+IL-6 conditioning produces the signature low frequency of CD11c$^{pos}$ cells which is also observed in vitro at the end of Flt3-L+IL-6 Step 1 conditioning. This is representative of four experiments.
Figure 15:
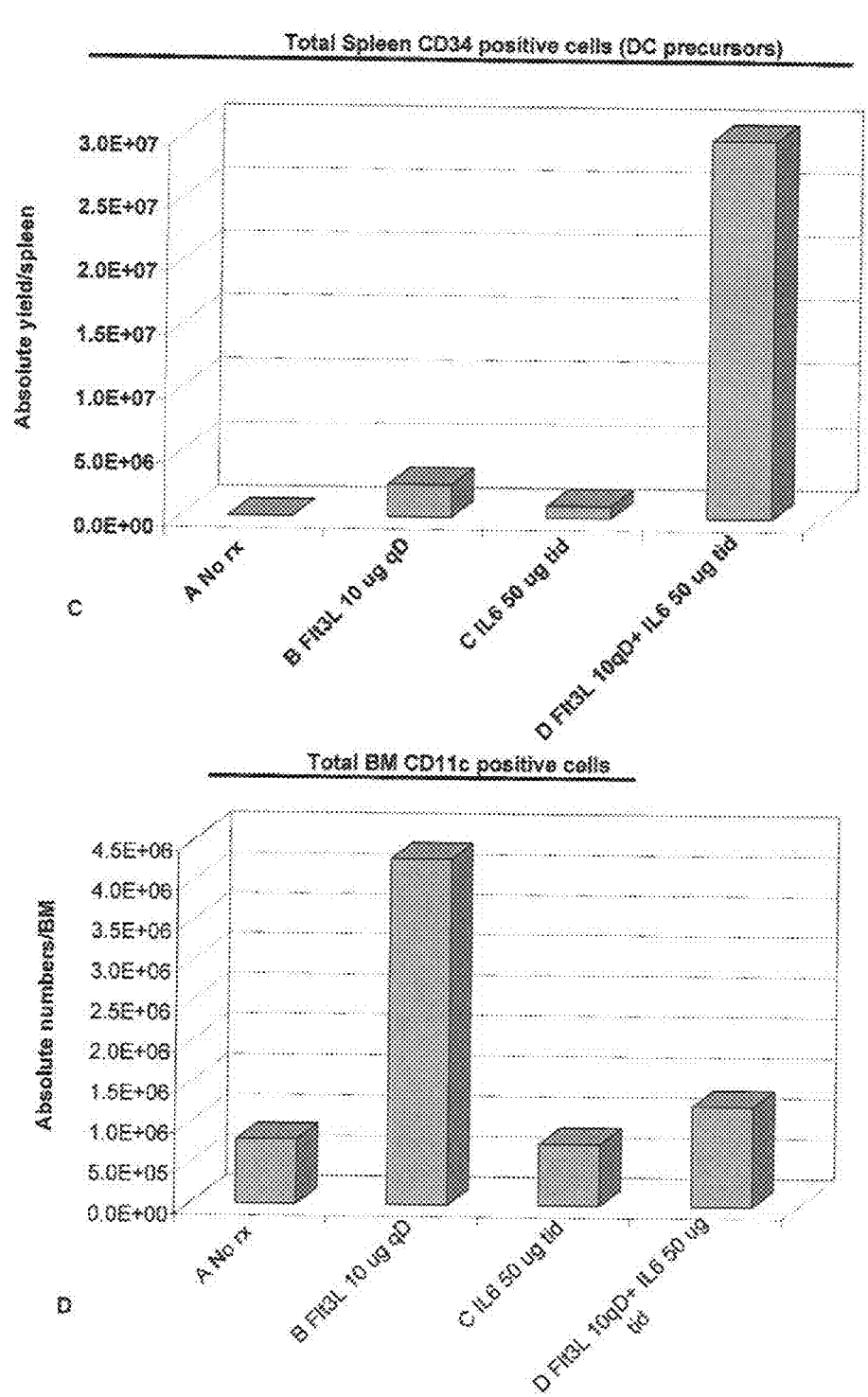
Figure 16:
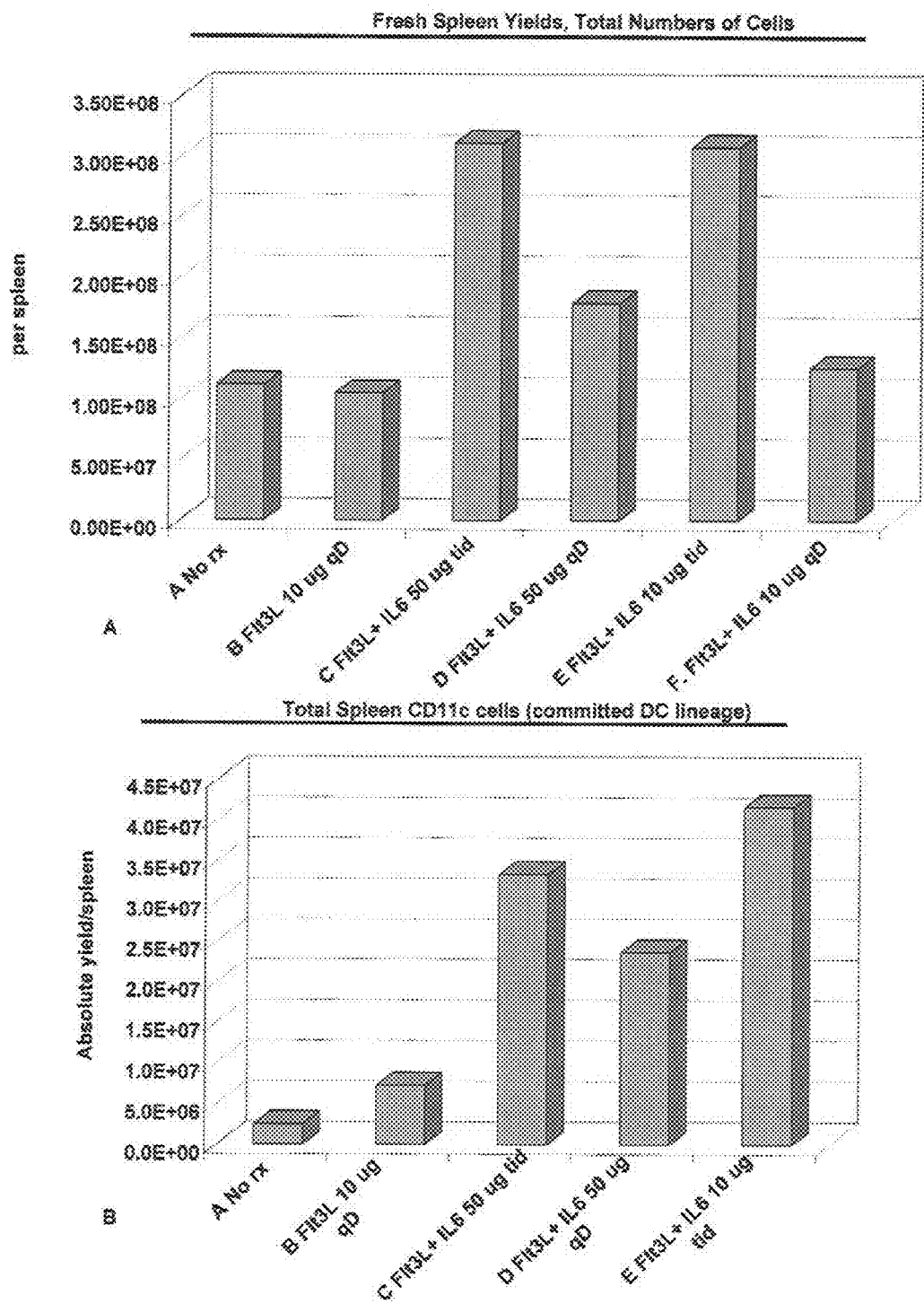
FIGS. 16A-D are a series of graphs showing BALB/c mice treated for six days with either (A) nothing, (B) rhFlt3-L 10 mcg i.p. daily, (C) rhFlt3-L 10 mcg i.p. daily plus rhIL-6 50 mcg i.p. three times daily, (D) rhFlt3-L 10 mcg i.p. daily plus rhIL-6 50 mcg i.p. once daily, (E) rhFlt3-L 10 mcg i.p. daily plus rhIL-6 10 mcg i.p. three times daily, and (F) rhFlt3-L 10 mcg i.p. daily plus rhIL-6 10 mcg i.p. once times daily. The next day mice were euthanized, spleens and BM harvested, and CD11c$^{pos}$ cells (committed DC lineage) and CD34$^{pos}$ cells (stem cells, potential DC precursors) quantified. Results are representative of three experiments. The data are consistent with the hypothesis that due to its short half-life, thrice daily administration of rhIL-6 is more effective than once daily, and 10 mcg dosing proved as effective as 50 mcg dosing.
Figure 16:
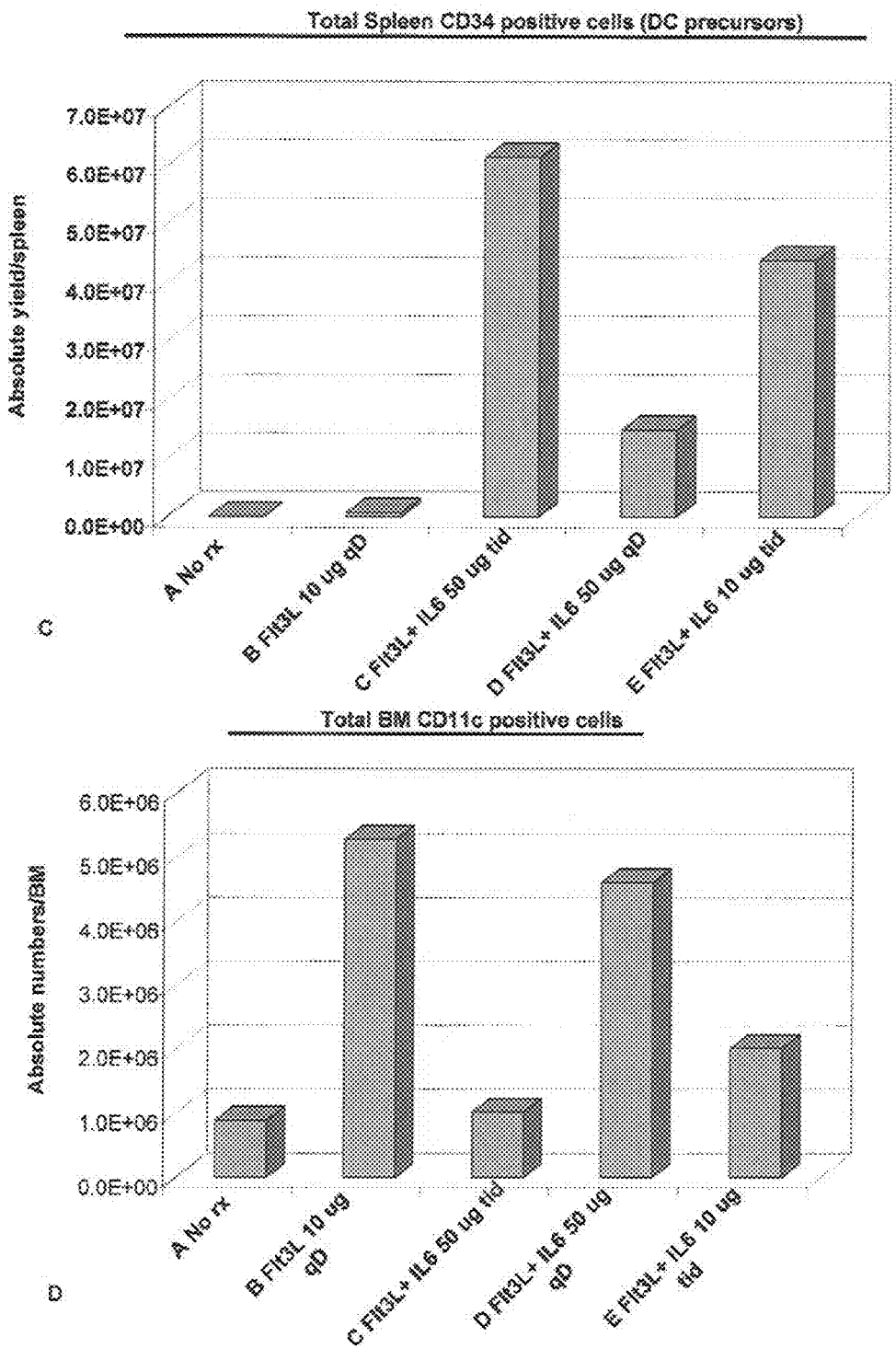
Figure 17:
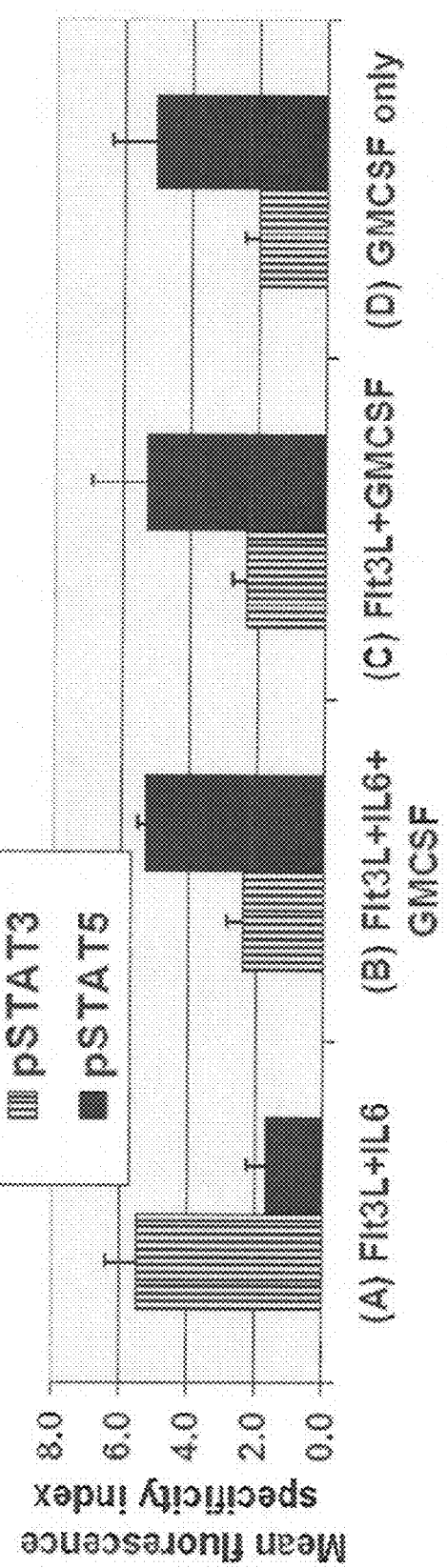
FIG. 17 illustrates the signature STAT activation patterns observed for each treatment and how they alternate between Step 1 and Step 2. Specifically.

Conditioned DC precursors were transferred to Step 2 culture, exposed to viable irradiated tumor, optionally further activated with CpG+LPS, then co-cultured with tolerized TDLN T cells from mice bearing the relevant tumor. Flt3L+ IL6 conditioned, tumor-pulsed DCs efficiently reversed tolerance and stimulated robust T cell proliferation, even when exogenous cytokines such as IL2 were not added to culture (FIG. 8A/FIG. 13. CpG+LPS treatment enhanced but was not essential for such efficacy (not shown). In contrast, DCs prepared after other conditioning treatments typically proved lethal to T cell co-cultures, and such toxicity could not be rescued by exogenous IL2, IL15 or IL7 (FIG. 8A/ FIGS. 13A-B). T cell cultures driven by Flt3L+IL6 conditioned DC Displayed superior outgrowth of both CD4$^+$ and CD8$^+$ tumor-specific T cells compared to anti-CD3 treatment, and were also highly potent when administered to tumor-bearing mice as adoptive therapy (FIG. 8B, FIG. 14).

Flt3L+IL6 BM Conditioning Similarly Impacts In Vivo Performance

Figure 9:
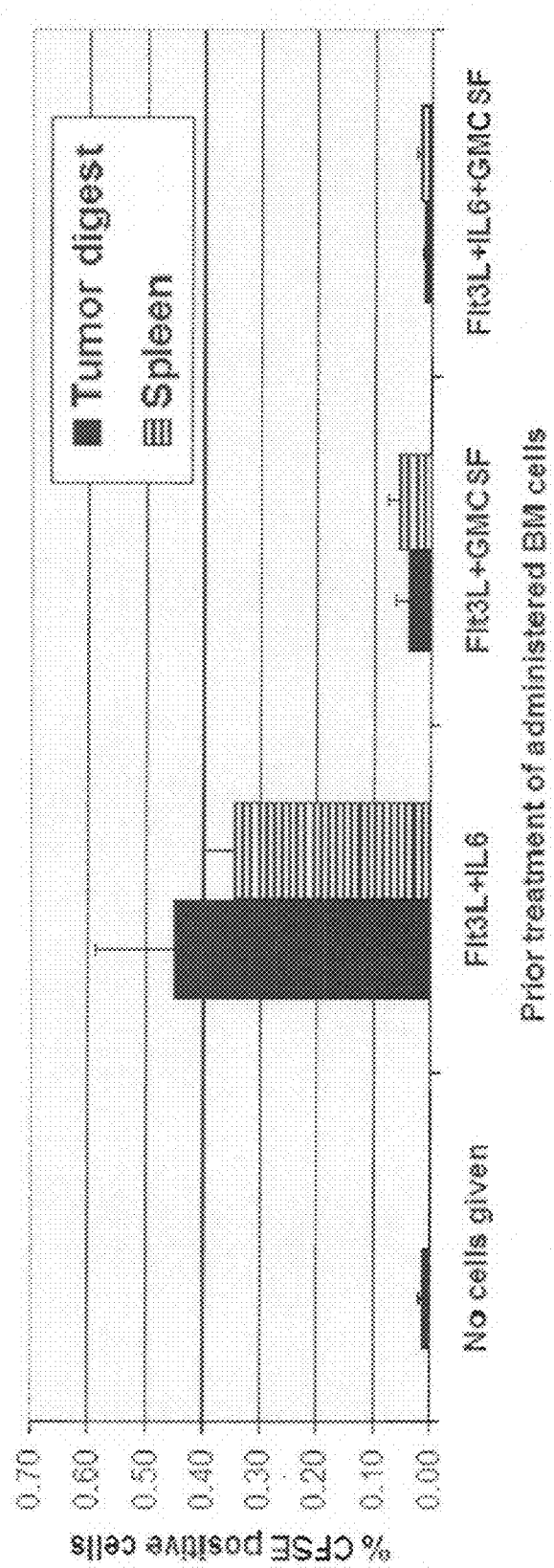
FIG. 9 is a histogram showing the in vivo fate of BM cells administered following Step 1 conditioning treatments. 18 million BM cells were labeled with CFSE and given by tail vein to mice bearing 10 day MCA-203 s.c. tumors. 48 h later, mice were euthanized and single cell suspensions of tumors and spleens processed for FACS analyses. Specifically.

We monitored the fates of CFSE-labeled BM cells administered to mice bearing 10 day tumors following various Step 1 culture treatments. BM cells administered i.v. immediately after Step 1 conditioning with Flt3L+GMCSF or Flt3L+ GMCSF+IL6 displayed a severely limited capacity to traffic into either tumor or spleen (FIG. 9). In contrast, Flt3L+IL6 conditioned BM cells displayed a consistent capacity to infiltrate both established tumors and spleen (FIG. 9). Such Flt3L+IL6 conditioned BM cells achieved essentially uniform DC differentiation following entry into either tumor or spleen. Furthermore, accelerated DC maturation was observed following entry into tumor compared to spleen, consistent with the observed impacts of tumor exposure in vitro during Step 2 culture.

TLR and IRF Expression Characteristics of Flt3L+IL6 Conditioned DCs

We characterized expression elements of the myeloid DCs which dominated Step 2 culture following Flt3L+IL6 conditioning. Expression of TLR3, TLR4, TLR7, TLR8 and TLR9 remained uniform on the cellular level at all stages of culture, functionally confirmed by these cells' broad responsiveness to respective TLR agonists. Interferon-regulatory factors IRF4 and IRF8 were dually expressed both by DC precursors and by the DCs themselves following DC1 polarization. Such phenotypic evidence indicated a largely homogeneous sequence of differentiation, maturation and polarization, without the induction of DCs displaying heterogeneous TLR or IRF expression (Naik, S H et al. *J. Immunol.* 174, 6592-6597 (2005)).

EXAMPLE 3

DCs can be preconditioned in order to promote later acquisition of clinically desirable characteristics. For example, maturation of monocyte-derived human DCs with IFNγ+LPS not only stimulates robust IL12p70 secretion, but also conditions for a even greater second burst of IL12p70 secretion if DCs experience CD40 ligation within several days (B. J. C. et al, "Induction of Lymphocytic Infiltrates, Humoral Immunity, and Tumor Immunoediting in Women with Early Breast Cancer Following HER-2/neu Pulsed-Dendritic Cell Vaccination with IL-12 burst secretion," submitted for publication). We here report that exposure of mouse BM to Flt3L+IL6 triggered a multilog expansion of $CD34^{pos}$ stem cells which were highly facilitated for subsequent DC differentiation. Such Flt3L+IL6 conditioning induced nearly uniform and maximal $CD34^{pos}$ cell responsiveness to conventional DC maturational stimuli; primed for a degree of spontaneous DC maturation even when signaling guidance was minimal; and could transform contact with tumor into a stimulus similar in impact to a single TLR agonist both in vitro and in vivo (Xu, S. et al. *J. Immunol.* 171, 2251-2261 (2003); Napolitani, G. et al. *Nat. Immunol.* 6, 769-776 (2005)).

The decisiveness with which Flt3L+IL6 conditioning subverted normal multilineage hematopoiesis into the generation of dedicated DC precursors suggests that this may represent a severe but appropriate host response to certain life threatening BM infections. Consistent with this hypothesis, Flt3L and IL6 are strongly induced by myelosuppression and BM inflammation, respectively (Chklovskaia, E. et al. *Blood* 93, 2595-2604 (1999); Gaugler, M H et al. *Br. J. Haematol.* 103, 980-989 (1998)). Natural conditioning of host BM with Flt3L+IL6 may ensure transient outgrowth of high performance DC precursors from a threatened stem cell pool, the efficiency for pathogen encounters bolstered by the licensing to achieve DC1 polarization somewhat independently of both stimulatory and regulatory signals. The potential therapeutic benefit of such DC licensing for anti-tumor immunity is apparent (FIGS. 8A-B/FIGS. 13A-B and FIG. 14).

Similar DC licensing occurred when Step 1 conditioning was performed with either Flt3L+IL6 or Flt3L alone. However, Flt3L-licensed DC precursors remained scant in number in the absence of co-conditioning by IL6 (FIG. 6). IL6 and its receptor transducing component gp130 have long been recognized to synergize for stem cell proliferation with receptor tyrosine kinase activating stimuli, including both c-kit ligand (SCF) and FLT3/FLK2 ligand (Flt3-L) (Ebihara, Y. et al. *Blood* 90, 4363-4368 (1997); Sui, X et al. *Proc. Natl. Acad. Sci.* 92, 2859-2863 (1995); Brasel, K. et al. *Blood* 90, 3781-3788 (1997); Hudak, S. et al. *Blood* 85, 2747-2755 (1995)), but the lineage outcomes of such proliferation are highly distinctive, with only Flt3L+IL6 giving rise to nearly uniform licensing of DC differentiation. Although GMCSF also synergized with Flt3L to induce Step 1 stem cell proliferation, in contrast to IL6 it was observed that GMCSF antagonized all of Flt3L's DC licensing effects. Therefore, IL6 proved exceptional in its capacity to provide both permissive signaling and proliferative synergy for Flt3L's DC licensing impact.

The mechanism(s) by which Flt3L+IL6 conditioned BM responds to tumor exposure as a DC maturational signal remains to be elucidated. Currently available data indicate that direct contact with particulate tumor is necessary, and that this is MHC independent. Based on these data, a plausible mechanism involves DC activation via putatively expressed lectin receptors such as asialoglycoprotein receptor (ASGPR) and DEC-205 (Bonifaz, L. et al. *J. Exp. Med.* 196, 1627-1638 (2002); Valladeau, J. et al. *J. Immunol.* 167, 5757-5774 (2001)), since identical or similar carbohydrate receptors are employed by tumoricidal macrophages to bind to and kill tumor cells nonantigenically (Cohen, P A et al. *Crit. Rev. Immunol.* 20, 17-56 (2000); Oda, S. et al. *J. Biochem. (Tokyo)* 105, 1040-1043 (1989)). It is well established that many tumor cells are bound by lectins much more avidly than non transformed cells, due to a chronically high density of exposed carbohydrates, coupled with a diminished presence of differentiation elements which may normally mask such carbohydrates (Oda, S. et al. *J. Biochem. (Tokyo)* 105, 1040-1043 (1989); Rapin, AM et al. *Adv. Cancer Res.* 20, 1-91 (1974)). We have observed that exposure to albumin crosslinked with mannose or N-acetyl-glucosamine can also accelerate the maturation of Flt3L+IL6 conditioned BM cells (not shown).

We are investigating the mechanism(s) by which certain proliferative conditioning treatments, notably SCF+IL6, Flt3L+GMCSF, and Flt3L+GMCSF+IL6, caused DC preparations to be highly toxic to T cell cultures, especially primary cultures. This lethal effect did not appear to be attributable to activation of regulatory T cells or indoleamine dioxygenase (IDO)-expressing pDC, since toxicity could not be remedied by adding exogenous IL2 to the co-cultures (Powell, D J et al. *J. Immunother.* 28, 403-411 (2005); Munn, D H et al. *J. Clin. Invest.* 114, 280-290 (2004)). There was, however, a general correlation between the $Gr1^{pos}$ cell inducing tendency of individual conditioning treatments and the observed lethal effects upon T cell cultures; therefore, it is possible that immature $Gr1^{pos}$ myeloid suppressor cells present in the DC preparations mediate the untoward effects of many of the conditioning treatments (Kusmartsev, S. et al. *J. Immunol.* 172, 989-999 (2004); Serafini, P. et al. *Cancer Res.* 64, 6337-6343 (2004)). In contrast, Flt3L+IL6 conditioned DC cultures were exceptional for their consistent absence of toxicity even when added to T cells in high proportions.

The above experiments, as well as preliminary studies with human $CD34^{pos}$ stem cells (not shown), support the hypothesis that Flt3L+IL6 may be an effective means to proliferate, condition and mobilize highly therapeutic DC precursors for tumor therapy. As noted above, occult production of IL6 has been implicated in the impacts of exogenous Flt3L upon BM cultures (Brasel, K. et al. *Blood* 90, 3781-3788 (1997)), and it has long been appreciated that IL6 has extremely potent therapeutic properties against established mouse tumors, even when administered as a single agent (Mule, J J et al. *J. Immunol.* 148, 2622-2629 (1992)). We postulate that the major mechanistic role and benefit of IL6 therapy will be in tandem with Flt3L to proliferate and condition improved DC precursor populations in cancer patients.

EXAMPLE 4

Mice and Tumors

Female C57BL/6N (B6), C3H/HeJ and BALB/c mice were purchased from the Biologic Testing Branch, Frederick Cancer Research and Developmental Center, National Cancer Institute (Frederick, MD). They were maintained in a specific pathogen-free environment and were used at the age of 8 to 12 weeks. The MCA 203, 105 and 205 fibrosarcomas and B16 melanoma, syngeneic to B6 mice, CT26 colonic adenocarcinoma, syngeneic to BALB/c mice, and the 888 mel human melanoma line were maintained as described previously (Peng, L. et al. *J. Immunol.* 169, 4811-4821 (2002); Parkhurst, MR et al. *J. Immunol.* 170, 5317-5325 (2003)).

Reagents rhFlt3-L was a generous gift of Amgen, Inc. (Thousand Oaks, Calif.). hIL2 was a generous gift of Chiron (Emeryville, Calif.) murine GMCSF was a generous gift from Immunex (Seattle, Wash.). Recombinant mouse stem cell factor (mSCF), mIL6, mIL10, mVEGF, mIL3, murine thrombopoeitin, mIL4, rmIFNγ, rhIL7 and rhIL15 were purchased from Peprotech (Rocky Hill, N.J.). rhTGFβ1 was purchased from R&D (Minneapolis, Minn.). PGE$_2$, LPS (*E. coli* 026: B6), poly I:C and prostaglandin E$_2$ were purchased from Sigma (St. Louis, Mich.). CpG (ODN 1826) and imiquimod were purchased from Invivogen (San Diego, Calif.). Standard culture medium (CM) consisted of RPMI-1640 with 10% heat deactivated FCS, plus 0.1 mM nonessential amino acids, 1 mM sodium pyruvate, 2 mM L-glutamine, 100 mg/ml streptomycin, 100 U/ml penicillin, 50 mg/ml gentamicin, 0.5 mg/ml Fungizone (all from Life Technologies, Grand Island, N.Y.), and 5×10$^5$ M 2-ME (Sigma) ((Peng, L. et al. *J. Immunol.* 169, 4811-4821 (2002)).

BM Processing and Proliferation (Step 1 of Culture)

Single cell suspensions were prepared from the femurs and tibias of healthy mice (Kuriyama, H. et al. Dev. Biol. (Basel) 116, 169-178 (2004)). Following RBC lysis by ammonium chloride, no further processing was performed. 12-15 million unfractionated BM cells (typical content of CD34$^{pos}$ cells 8-12%) were cultured at 0.5 million/ml in 75 cm$^2$ flasks (Corning, N.Y.) in CM with the factors to be tested: hFlt3L 25 ng/ml (similar results up to 300 ng/ml); mIL6 25 ng/ml (similar results up to 100 ng/ml, 100 ng/ml rhIL6 was also effective); mSCF 25 ng/ml (similar results up to 100 ng/ml, rSCF was also effective); rmGMCSF 10 ng/ml (similar results up to 25 ng/ml); rmIL4 10 ng/ml (similar results up to 25 ng/ml). Recombinant thrombopoeitin, IL3 and fibronectin were also assessed but had negligible superimposed proliferative impacts (not shown). BM cells were normally cultured for 6-7 days, harvested, counted, and washed twice in PBS prior to initiation of Step 2 cultures.

In Vitro Differentiation of BM Cells (Step 2 of Culture)

Step 2 was initiated (0 hr) in CM, rmGMCSF and optionally rmIL4. Step 2 cultures were performed in 24 well cluster plates, 4 million BM cells per well in 2 ml CM. DC1 polarization stimuli such as CpG (ODN 1826, 5 µM) and LPS 50 ng/ml were added between 18-24 hrs, and cells harvested at 40-44 hrs for analyses. When included, immunosuppressive agents rmIL10, rmVEGF, rhTGFβ1 or PGE$_2$ were added between 0 and 24 hrs of Step 2 culture at doses specified in Results. Alternatively, particulate tumor cells, either viable unirradiated, viable irradiated (10,000 cGy), or killed freeze-thawed lysate (Cohen, P A et al. Cancer Res. 54, 1055-1058 (1994)), were added to Step 2 BM cells. Viable tumor cells were sometimes labelled with CFSE (Molecular Probes, Eugene, Oreg.) to allow their identification and exclusion during subsequent FACS analyses (Peng, L. et al. *J. Immunol.* 169, 4811-4821 (2002)).

FACS Analyses of Cultured BM Cells

For routine multicolor FACS analyses, BM cells were cultured in anti-CD32 mAb plus normal mouse IgG to block FcRs, then directly stained with conjugated specific mAbs or isotype controls as listed in the figures (BD-Pharmingen, Mountain View, Calif.) (Peng, L. et al. *J. Immunol.* 165, 5738-5749 (2000)). When additionally assessing IL12 production at the cellular level, the last 16 hrs of Step 2 culture were performed in monensin (Golgistop™, BD-PharMingen). Then, following FcR block and direct staining of surface molecules, cells were fixed in formalin and permeabilized in tween (CytoPerm/CytoFix™, PharMingen), then additionally stained with PE-anti-mouse IL12p40 (BD-Pharmingen) or isotype control.

Intracellular staining for TLR was performed directly on fixed, permeabilized cells with conjugated mAb (TLR3, TLR4, TLR8, TLR9), or indirectly with unconjugated mAb (TLR7), and appropriate controls from Imgenix (San Diego, Calif.). Staining of fixed, permeabilized cells for intracellular IRF4 and IRF8 was performed with reagents from Santa Cruz Biotechnology (Santa Cruz, Calif.) and mouse adsorbed F(ab)'$_2$ fragments of donkey anti-goat Ab (Research Diagnostics, Inc, Concord, Mass.), following the method of Tamura et al (Tamura, T. et al. *J. Immunol.* 174, 2573-2581 (2005)).

To isolate CD34$^{pos}$ and CD34$^{neg}$ cells from freshly harvested BM, the latter were dually stained with FITC-rat anti-mouse CD34$^{pos}$ and PE-Rat IgG2a isotype Ctrl Ig (dialyzed to remove sodium azide), then sorted on a FACSAria. Double positive cells were scored as potentially falsely positive for CD34 expression and excluded from collection, enabling isolation of >96% pure CD34$^{pos}$ and CD34$^{neg}$ subpopulations.

ELISAs

Assessments of supernatant contents of mIL12p70 heterodimer were performed with BD-Pharmingen reagents. mIFNα and mIFNβ ELISAs were performed with kits from PBL Biomedical Laboratories (New Brunswick, N.J.).

T Cell Co-Cultures

Prior to harvest of T cells from tumor-bearing mice, DCs were prepared under various Step 1 conditions in CM; Step 2 was performed in 1% non heat-deactivated mouse serum instead of FCS (CM-MS), during which BM cultures were exposed to viable irradiated tumor cells, then CpG+LPS as denoted in Results. On the day of DC harvest, T cells were freshly harvested from the tumor-draining lymph nodes of mice bearing 12 day tumors. The L-selectin$^{low}$ (tolerized pre-effector) fraction of T cells was isolated by negative selection as described previously (Peng, L. et al. *J. Immunol.* 165, 5738-5749 (2000); Wang, L. et al. *J. Translational Med.* 2, 41 (2004)), and cultured in CM-MS with immobilized anti-CD3 (Peng, L. et al. *J. Immunol.* 165, 5738-5749 (2000); Wang, L. et al. *J. Translational Med.* 2, 41 (2004)) or variously conditioned DCs. Beginning on day 2 of T cell culture, some groups also received rhIL2 (24 I.U./ml), or rhIL2, rhIL7 (50 ng/ml) and rhIL15 (5 ng/ml). T cells were harvested for assays and adoptive therapy after 12 days of culture.

T Cell Specificity Assays (Intracellular IFNγ)

Cultured T-cells were harvested and re-plated in fresh CM-MS at 2 million T-cells per well in 24 well plates. Whole cell tumor digests, irradiated to 5000 cGy, were added at 2 million cells/well as stimulators. Co-culture proceeded for 18 h, with monensin added 5 hrs into culture. At harvest, individual treatment groups were FcR-blocked, then stained with FITC-anti-CD4 and Cychrome (Cy)-anti-CD8. Following fixation, cells were additionally stained with PE-anti-mouse IFNγ or isotype controls, and then analyzed.

Adoptive Immunotherapy

To establish intradermafl tumors in healthy syngeneic mice, 1.5 million viable tumor cells were injected into the midline ventral skin (Peng, L. et al. *J. Immunol.* 165, 5738-5749 (2000)). 5 or 10 days after tumor inoculation, mice received conventional nonmyeloablative whole body irradiation (WBI, 500 cGy) (Peng, L. et al. *J. Immunol.* 165, 5738-5749 (2000)), followed by infusion of culture-activated T-cells by tail vein. Perpendicular bi-dimensional tumor measurements were performed twice weekly. Mice were euthanized when tumor diameter exceeded 15 mm to avoid unacceptable morbidities. Survival among treatment groups was compared by the Mann-Whitney rank sum test. Individual mice were scored for final treatment outcome (lethal tumor vs cure) and treatment groups compared. A two-tailed p value <0.05 was deemed significant.

In Vivo Monitoring of BM Cells

At the ends of Step 1 or Step 2 cultures, BM cells were labeled with CFSE (Peng, L. et al. *J. Immunol.* 169, 4811-4821 (2002)) and injected by tail vein into syngeneic mice bearing 10 day s.c. MCA-203 or MCA-105 tumors. 48 h later, mice were euthanized, tumors harvested and enzymatically digested to produce whole cell digests, with spleen cell suspensions prepared in parallel (Peng, L. et al. *J. Immunol.* 169, 4811-4821 (2002)). Tumors and spleens from individual mice were analyzed by FACS for CFSE$^{pos}$ cell content and treatment outcomes compared by Student's t-test. Groups were then co-stained with PE-conjugated mAb against DC-associated surface determinants, and FACS acquisition gated to analyze the CFSE$^{pos}$ subpopulation.

EXAMPLE 5

We examined how STAT knockout BM preparations responsed to Flt3L+IL-6 conditioning. Consistent with STAT3's putative obligate role in Flt3-L-induced DC differentiation, we observed that STAT3KO BM did not survive Flt3-L+IL-6 conditioning (not shown). In contrast, STAT5KO BM responded to Flt3-L+IL-6 conditioning with intact robust proliferation and nearly uniform DC differentiation during subsequent Step 2 culture. Nonetheless, compared to wildtype littermates, Flt3-L+IL-6 conditioned STAT5KO DCs displayed submaximal phenotypic maturation and IL-12p70 production (FIG. 1). Therefore, the proliferative and differentiative impacts of Flt3-L+IL-6 conditioning were absolutely STAT3-dependent, whereas final phenotypic maturation and DC1-polarization were at least partially STAT5-dependent.

Figure 18:
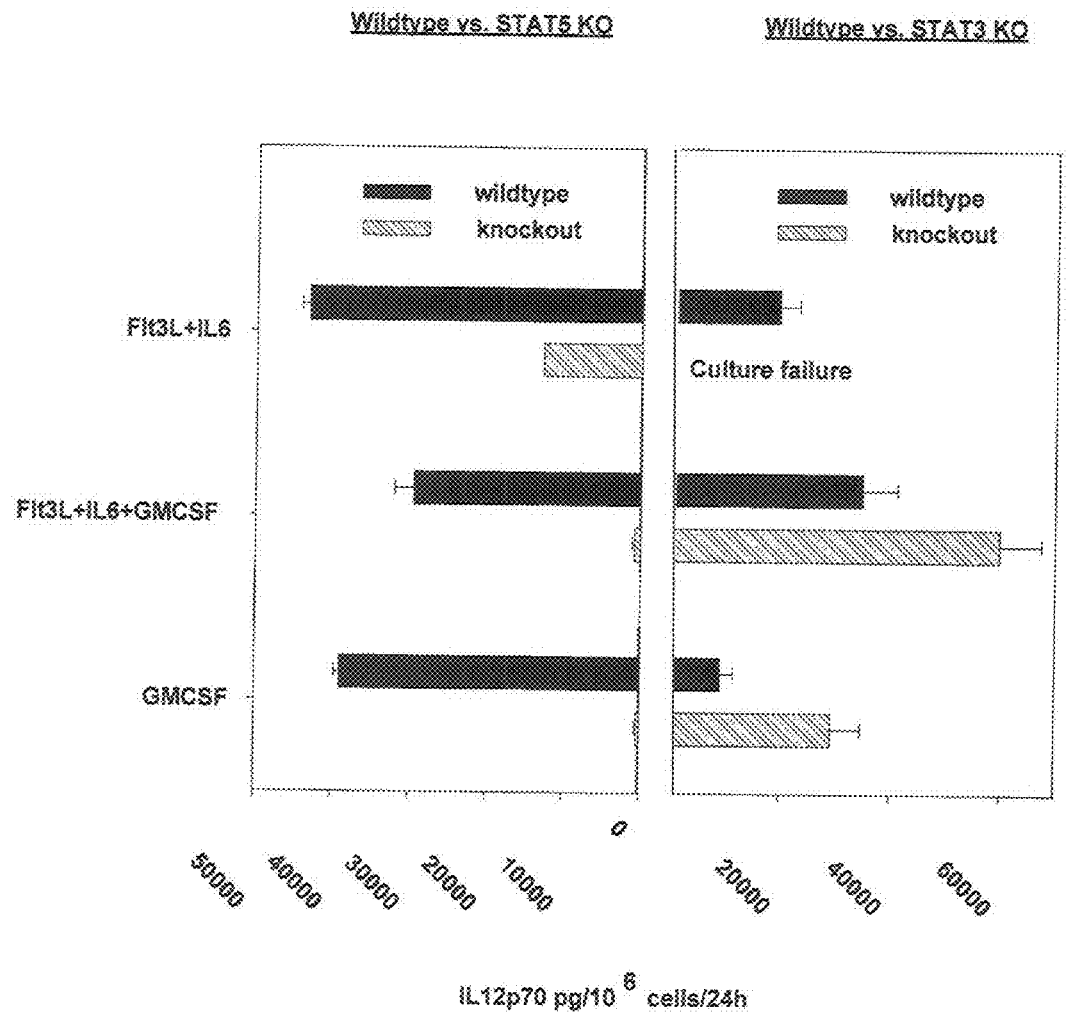
FIG. 18 illustrates responses of STAT knockout vs. wild-type littermate BM to Flt3-L+IL-6 vs. GMCSF-containing conditioning regiments. Specifically.

We also examined how STATKO BM preparations responded to GMCSF-containing Step 1 regimens (GMCSF alone, Flt3-L+GMCSF, or Flt3-L+GMCSF+IL-6). All of these GMCSF-based conditioning regimens were strikingly ineffective for generating DCs from STAT5KO BM, instead yielding predominately Gr-1$^{pos}$, MHC Class II$^{neg}$ cells with the morphologic features of mature neutrophils. In contrast, STAT3KO BM displayed normal proliferation kinetics (not shown) and typical heterogeneous differentiation, including DC differentiation, in response to all GMCSF-based regimens. Following GMCSF-based conditioning, however, STAT3KO DCs displayed an abnormally heightened maturational and IL-12p70 response to TLR stimulation (FIG. 18 right). Therefore, all tested GMCSF-containing regimens promoted STAT5-dependent DC differentiation, with later phenotypic maturation and DC1-polarization proving susceptible to inhibition through STAT3.

From the above description of the invention, those skilled in the art will perceive improvements, changes and modifications. For example, known cell therapy methods may be used to deliver DC precursor cells, mature DCs, and/or combinations thereof to a subject. Such improvements, changes and modifications within the skill of the art are intended to be covered by the appended claims. All references, publications, and patents disclosed above are herein incorporated by reference in their entirety.

Having described the invention, we claim:

1. A method of generating a population of dendritic cell (DC) precursors, the method comprising the steps of:
   obtaining bone marrow from the subject, the bone marrow including CD34$^{pos}$ progenitor cells from a subject;
   culturing the progenitor cells in a culture medium including Flt3 ligand (Flt3-L), interleukin-6 (IL-6), and a STAT5 antagonist, and being free of granulocyte-macrophage colony-stimulating factor (GMCSF), the progenitor cells being cultured for a time and under conditions effective to allow the progenitor cells to differentiate into DC precursors having a surface marker phenotype B220$^{pos}$CD11c$^{neg}$/MHC Class II$^{neg}$; and
   selecting the B220$^{pos}$/CD11c$^{neg}$/MHC Class II$^{neg}$DC precursors from the culture.

2. The method of claim 1, the progenitor cells being cultured for a time and under conditions sufficient to allow the progenitor cells to differentiate into DC precursors having a surface marker phenotype B220$^{pos}$/CD11c$^{neg}$/MHC Class II$^{neg}$CD45RA$^{pos}$.

3. The method of claim 1, wherein the culture medium further comprises SCF.

4. A method of generating a population of dendritic cell (DC) precursors, the method comprising the steps of:
   obtaining CD34$^{pos}$ progenitor cells from a subject;
   culturing the progenitor cells in a culture medium that includes Flt3 ligand (Flt3-L), interleukin-6 (IL-6), and a STAT5 antagonist, and being free of granulocyte-macrophage colony-stimulating factor (GMCSF), the progenitor cells being cultured in the culture medium for a time and under conditions effective to allow the progenitor cells to differentiate into DC precursors having a surface marker phenotype B220$^{pos}$/CD11c$^{neg}$/MHC Class II$^{neg}$; and
   selecting the B220$^{pos}$/CD11c$^{neg}$/MHC Class II$^{neg}$ DC precursors from the culture.

5. The method of claim 4, the progenitor cells being cultured for a time and under conditions sufficient to allow the progenitor cells to differentiate into DC precursors having a surface marker phenotype B220$^{pos}$/CD11c$^{neg}$/MHC Class II$^{neg}$/CD45RA$^{Pos}$.

6. The method of claim 4, the culture medium further including SCF.

7. The method of claim 4, the progenitors cells being isolated from bone marrow of the subject.

* * * * *